(12) United States Patent
Shyu et al.

(10) Patent No.: US 10,988,733 B2
(45) Date of Patent: *Apr. 27, 2021

(54) METHODS FOR OBTAINING PLURIPOTENT ADULT OLFACTORY STEM CELLS FROM AN OLFACTORY MUCOSA TISSUE

(71) Applicant: China Medical University, Taichung (TW)

(72) Inventors: Woei-Cherng Shyu, Taichung (TW); Chung-Y. Hsu, Taichung (TW); Der-Yang Cho, Taichung (TW); Chen-Huan Lin, Taichung (TW); Wei Lee, Taipei (TW); San-Yuan Chen, Hsinchu (TW); Long-Bin Jeng, Taichung (TW); Chang-Hai Tsai, Taichung (TW)

(73) Assignee: China Medical University, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,056

(22) Filed: May 19, 2020

(65) Prior Publication Data

US 2020/0277569 A1 Sep. 3, 2020

Related U.S. Application Data

(62) Division of application No. 15/614,634, filed on Jun. 6, 2017, now Pat. No. 10,696,945.

(30) Foreign Application Priority Data

Dec. 30, 2016 (TW) ................................. 105144267

(51) Int. Cl.
C12N 5/071 (2010.01)
C12N 5/074 (2010.01)
(Continued)

(52) U.S. Cl.
CPC ............ *C12N 5/0607* (2013.01); *A61K 35/30* (2013.01); *A61K 35/545* (2013.01); *C12N 5/062* (2013.01); *C12N 5/0623* (2013.01); *A01K 2267/03* (2013.01); *A01K 2267/0318* (2013.01); *A61K 35/12* (2013.01); *A61K 2039/6006* (2013.01); *C12N 5/00* (2013.01); *C12N 5/06* (2013.01); *C12N 5/0602* (2013.01); *C12N 5/0618* (2013.01); *C12N 5/0619* (2013.01); *C12N 5/0625* (2013.01); *C12N 5/0632* (2013.01); *C12N 5/0688* (2013.01); *C12N 5/0695* (2013.01); *C12N 5/0696* (2013.01); *C12N 2502/00* (2013.01); *C12N 2502/03* (2013.01); *C12N 2502/08* (2013.01); *C12N 2502/083* (2013.01); *C12N 2502/088* (2013.01); *C12N 2502/09* (2013.01); *C12N 2502/27* (2013.01); *C12N 2502/45* (2013.01); *C12N 2506/03* (2013.01); *C12N 2506/08* (2013.01); *C12N 2506/09* (2013.01); *C12N 2506/27* (2013.01); *C12N 2506/45* (2013.01); *C12N 2513/00* (2013.01); *C12N 2533/00* (2013.01); *C12N 2535/00* (2013.01); *C12N 2537/00* (2013.01); *C12N 2539/00* (2013.01); *G01N 33/48* (2013.01); *G01N 33/483* (2013.01); *G01N 33/50* (2013.01); *G01N 33/5005* (2013.01); *G01N 33/5008* (2013.01); *G01N 33/5023* (2013.01); *G01N 33/5044* (2013.01); *G01N 33/5058* (2013.01); *G01N 33/5073* (2013.01)

(58) Field of Classification Search
CPC ............ A61K 35/12; A61K 2039/6006; A61K 35/30; A61K 35/545; C12N 2506/08; C12N 15/85; C12N 5/0607; C12N 5/0619; C12N 5/0623; C12N 2506/03; C12N 5/0611; C12N 5/0618; C12N 2502/02; C12N 2502/04; C12Q 2600/106; C12Q 2600/158; G01N 33/6896; A01K 2227/105; A01K 2267/0312; A01K 2267/0318

See application file for complete search history.

(56) References Cited

U.S. PATENT DOCUMENTS

8,329,166 B2 * 12/2012 Li ........................... A61K 35/30
424/93.7
8,945,848 B2 * 2/2015 Shekdar ............. G01N 33/5061
435/6.13

(Continued)

FOREIGN PATENT DOCUMENTS

CN 102191221 A 9/2011
WO 2010127367 A2 11/2010

OTHER PUBLICATIONS

Fan et al. Cell Death & Disesae, 2018; 9:502.DOI 10.1038/s41419-018-0519-8.*

(Continued)

*Primary Examiner* — Chang-Yu Wang

(57) ABSTRACT

A method for obtaining a plurality of pluripotent adult olfactory stem cells (APOSCs) includes isolating the APOSCs, culturing the isolated APOSCs in a sphere culture medium, and collecting the cultured APOSCs that express Bmi-1 (B-lymphoma moloney murine leukemia virus insertion region-1), Oct-4 (Octamer-binding transcription factor 4), Sox-2 (Sex-determining region Y (SRY)-box 2), Nanog, SSEA-4 (Stage-specific embryonic antigen-4), ki67, c-Myc, KLF-4 (Kruppel Like Factor 4), K14 (Cytokeratin 14) and ICAM-1 (Intercellular Adhesion Molecule 1).

3 Claims, 31 Drawing Sheets

(21 of 31 Drawing Sheet(s) Filed in Color)

(51) Int. Cl.

| | |
|---|---|
| *C12N 5/0797* | (2010.01) |
| *C12N 5/0793* | (2010.01) |
| *C12N 5/079* | (2010.01) |
| *C12N 5/00* | (2006.01) |
| *C12N 5/0789* | (2010.01) |
| *A61K 48/00* | (2006.01) |
| *A61K 35/30* | (2015.01) |
| *A61K 35/545* | (2015.01) |
| *A61K 39/00* | (2006.01) |
| *G01N 33/50* | (2006.01) |
| *G01N 33/483* | (2006.01) |
| *G01N 33/48* | (2006.01) |
| *C12N 5/095* | (2010.01) |
| *C12N 5/07* | (2010.01) |
| *A61K 35/12* | (2015.01) |

(56) References Cited

U.S. PATENT DOCUMENTS

| | | | |
|---|---|---|---|
| 10,696,945 B2* | 6/2020 | Shyu | A61K 35/30 |
| 2012/0114616 A1 | 5/2012 | Adra | |
| 2012/0207744 A1* | 8/2012 | Mendlein | C12N 15/111 |
| | | | 424/130.1 |

OTHER PUBLICATIONS

Schnittke Doctor Disseratation: Smell you Later:Establishing and Activating Dorman, Reserve Stem cells in the Olfactory epithelium May 2014, Tufts Univeristy, Sackler School of Graduate Biomedical Science.*

Brann et al. Front. in Neurosci. 2014; doi:10.3389/fnins.2014.00182.*

Vavendano disseratation—English translated, "Potential for Self-Renewal and Stem cell quiescence hematopoietic derived from umbilical cord blood subjected in vitro to a leukemic niche microenvironment", 2017, Dept Physiol. Sci. National University of Colombia, Bogota DC. Colombia.*

Goldstein et al. Development 2018; 143:4394-4404 doi.10.1242/dev.142633.*

Murrell et al. Dev. Dyna. 2005; 233:496-515.*

Muniswami et al. Neural Regen. Res. 2017; 12:1895-1904, doi:10.4103/1673-3374.219052.*

Iwai et al., Stem Cells, 2008; 26:1298-1306.*

Chen et al. J. Comp. Neurol. 2004; 469:457-474.*

Carter et al. J. Neurosci. 2004; 24:5670-5683.*

Leung et al. Nat. Neursoc. 2007; 10:720-726.*

Gil et al.,Trends in Biochem. Sci.2018; 43:747-748.*

Mikhailova, Doctoral Disseration, 2016, University of Tempere, Finland.*

Goldstein, Bradley J., et al., "Contribution of Polycomb group proteins to olfactory basal stem cell self-renewal in a novel c-KIT+ culture model and in vivo", Development, published on Nov. 29, 2016, vol. 143, issue 23, pp. 4394-4404, published by The Company of Biologists Ltd., United Kingdom.

* cited by examiner

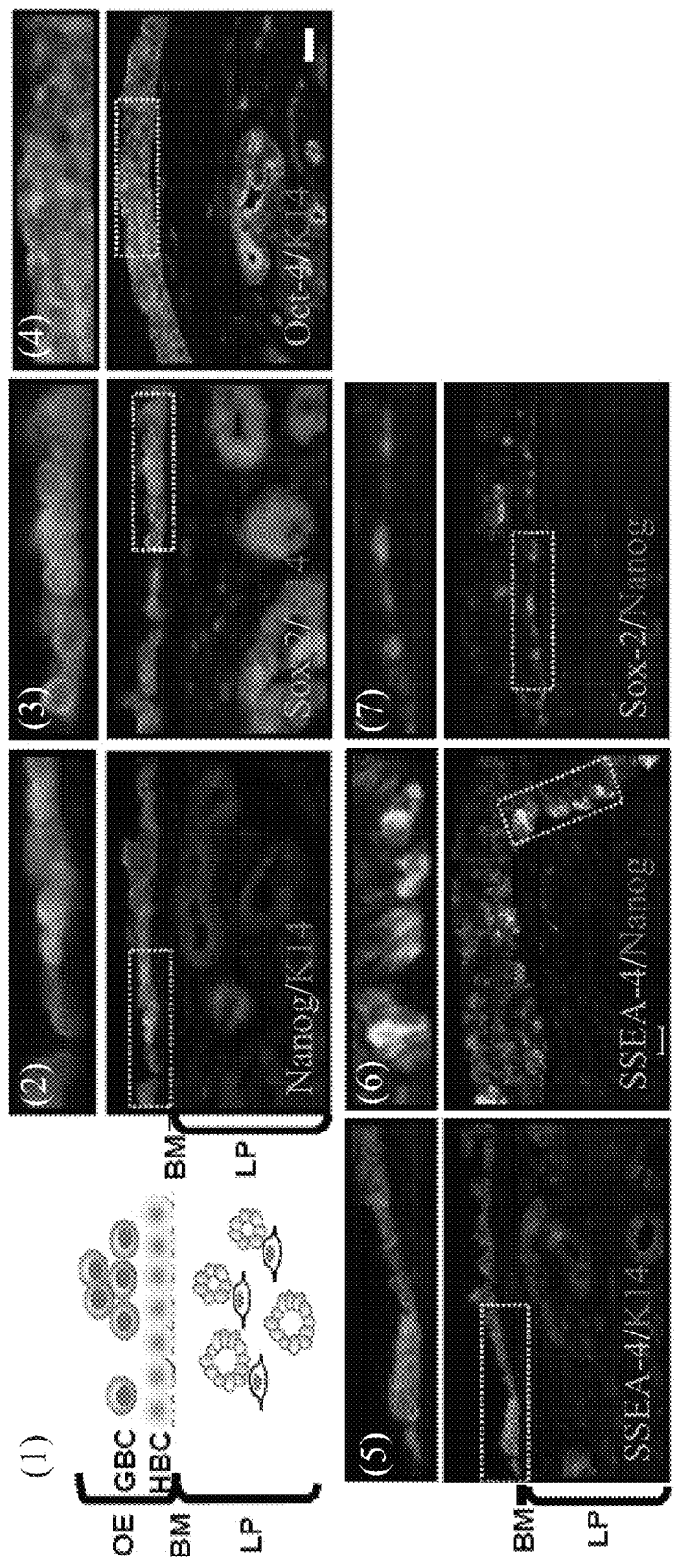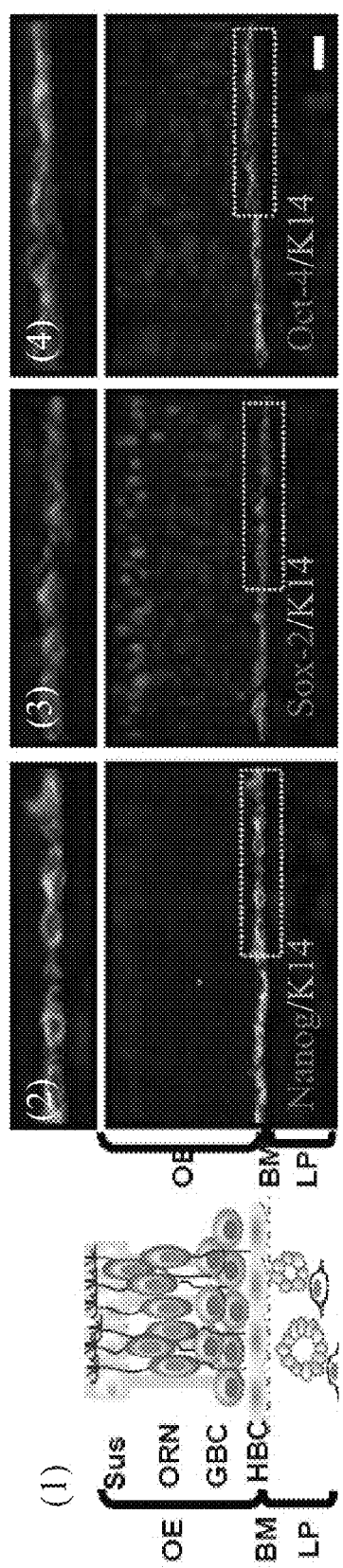
Fig. 6A
Fig. 6B

METHODS FOR OBTAINING PLURIPOTENT ADULT OLFACTORY STEM CELLS FROM AN OLFACTORY MUCOSA TISSUE

RELATED APPLICATIONS

The present application is a Divisional Application of the application Ser. No. 15/614,634, filed Jun. 6, 2017, U.S. Pat. No. 10,696,945 issued on Jun. 30, 2020, which claims priority to Taiwan Application Serial Number 105144267, filed Dec. 30, 2016, which is herein incorporated by reference.

BACKGROUND

Technical Field

The present disclosure relates to an undifferentiated animal cell. More particularly, the present disclosure relates to an adult stem cell.

Description of Related Art

Stem cells are undifferentiated primary cells that have abilities to duplicate and self-renew for long periods of time and differentiate into mature cells with specialized cell type and function. The stem cells can be classified into embryonic stem cells (ESCs) and adult stem cells according to their origin. The ESCs can be obtained from an inner cell mass of a blastocyst, and the adult stem cells can be obtained from various tissues. The stem cells can be further classified into totipotent stem cells, pluripotent stem cells, and multipotent stem cells according to their pluripotent ability. The totipotent stem cells have a full differentiation capability to develop into a complete embryo or an organism. The pluripotent stem cells have the potential to differentiate into three germ layers and then differentiate into almost any cells in a tissue or an organ, but the pluripotent stem cells are unable to develop into the complete embryo or the organism. The multipotent stem cells are the stem cells of specialized tissues, such as neural stem cells, hematopoietic stem cells, hepatic stem cells, and epidermal stem cells.

Because the pluripotent stem cells can differentiate into different cell lines, they can be used to treat a variety of degenerative diseases or genetic diseases. The ESCs are considered to have the above functions among the various pluripotent stem cells. Nevertheless, ethical concerns obstruct uses of human ESCs in research and treatment, while other pluripotent stem cells except the ESCs can avoid this obstruct. The pluripotent stem cells except the ESCs include bone marrow mesenchymal stem cells and umbilical cord blood stem cells. However, clinical applications of these pluripotent stem cells are limited by the need for in vitro expansion and the conditions of human leukocyte antigen pairing. Therefore, it needs to look for another pluripotent cell.

Adult stem cells refer to undifferentiated cells presented in differentiated tissues, which are presented in various tissues and organs of the body. Previously adult stem cells are thought that they only proliferate and differentiate into the cell types of the organ from which they originate. However, recent research results have questioned the traditional concept by pointing out that the adult organization contains stem cell populations having multiple differentiation ability. It is a good new that the adult stem cells can be used in medical applications, because it can replace the ethically controversial human ESCs. Accordingly, finding adult stem cells with self-renewal and pluripotency differentiation ability from the adult tissues becomes one of the main topics in the stem cell medical technology research and development.

SUMMARY

In one aspect, a method for obtaining a plurality of pluripotent adult olfactory stem cells (APOSCs) is provided. The APOSCs is isolated including (a) obtaining an olfactory tissue of a mammal, (b) culturing the olfactory mucosa tissue obtained from step (a) in a medium containing Dulbecco's Modified Eagle Medium/F12 (DMEM/F12 medium), heparin, bFGF, EGF and an antibiotic for 5-7 days to allow for migration of the cells from the cultured tissue, and (c) isolating adherent cells from step (b). The isolated APOSCs are cultured in a sphere culture medium comprising DMEM/F12 medium, B27 supplement, bFGF, EGF and an antibiotic. The cultured APOSCs that express Bmi-1 (B-lymphoma moloney murine leukemia virus insertion region-1), Oct-4 (Octamer-binding transcription factor 4), Sox-2 (Sex-determining region Y (SRY)-box 2), Nanog, SSEA-4 (Stage-specific embryonic antigen-4), ki67, c-Myc, KLF-4 (Kruppel Like Factor 4), K14 (Cytokeratin 14) and ICAM-1 are collected.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows:

FIG. 6A shows in vivo distribution analytical results of the human APOSCs;

FIG. 6B shows in vivo distribution analytical results of the mouse APOSCs;

DETAILED DESCRIPTION

Figure 1A:
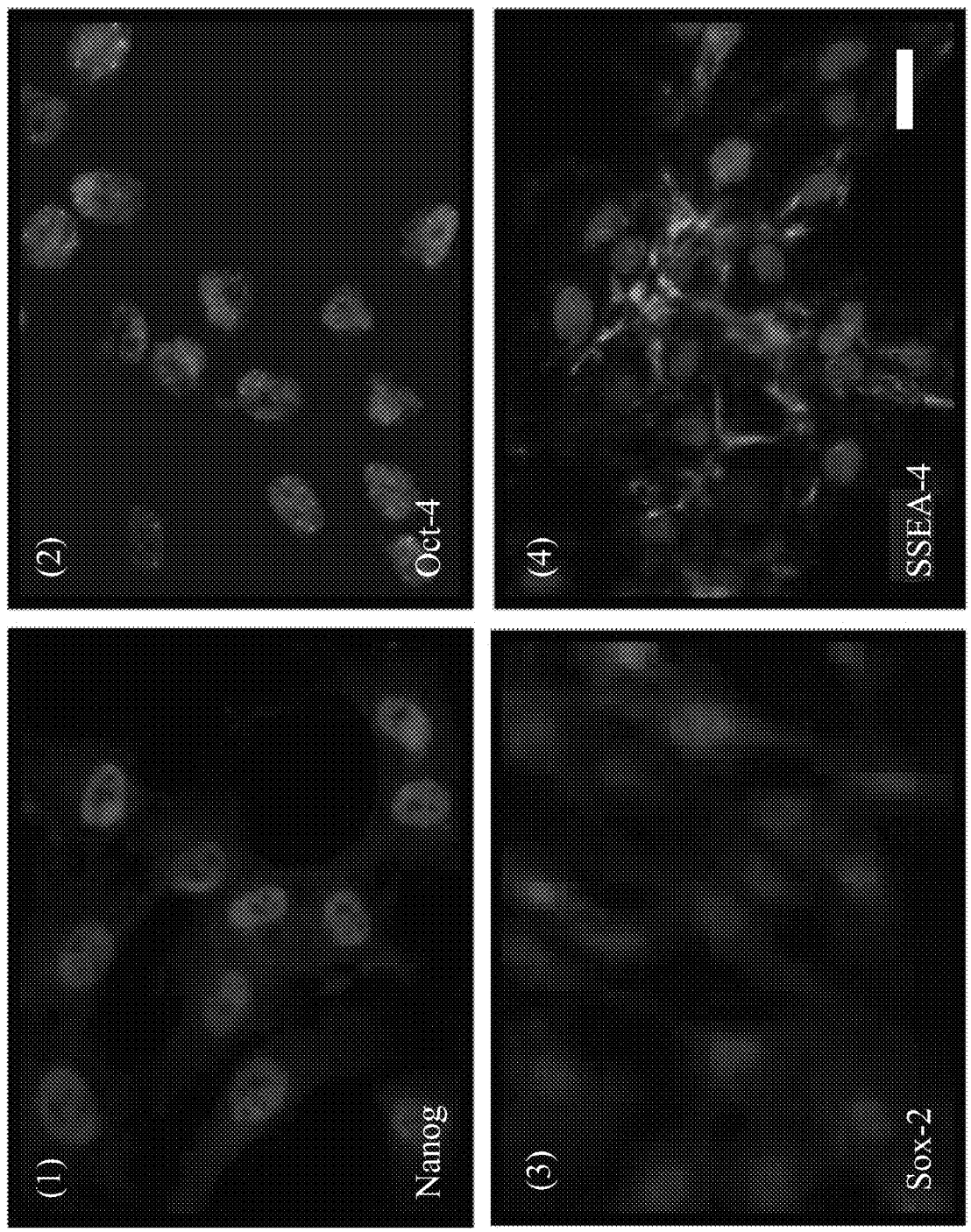
FIGS. 1A to 1C show analytical results of pluripotent markers expressions of the adult pluripotent olfactory stem cells isolated from human olfactory mucosa tissues (human APOSCs)

An adult pluripotent olfactory stem cell (APOSC) expressing a special cell receptor is provided. The APOSC has a self-renewal capability and a pluripotent capability. A method for obtaining a plurality of pluripotent adult olfactory stem cells is further provided. The method can quickly and specifically screen the adult olfactory stem cells having the pluripotent capability from an olfactory tissue of a mammal cell mixture.

In more details, aforementioned APOSC isolated from the mammal expresses Bmi-1 (B-lymphoma moloney murine leukemia virus insertion region-1). The APOSC can be isolated from a human or a murine; especially the APOSC can further express Oct-4 (Octamer-binding transcription factor 4), Sox-2 (Sex-determining region Y (SRY)-box 2), Nanog and SSEA-4 (Stage-specific embryonic antigen-4). The method for obtaining a plurality of the pluripotent adult olfactory stem cells includes isolating Oct-4 positive, Sox-2 positive, Nanog positive and SSEA-4 positive cells from the cell mixture of the olfactory tissue of the mammal to obtain the pluripotent adult olfactory stem cells. The method for obtaining a plurality of the pluripotent adult olfactory stem cells can further isolate Bmi-1 positive cells from the cell mixture of the olfactory tissue of the mammal to obtain the pluripotent adult olfactory stem cells. The mammal can be the human or the murine.

The isolated APOSC of the present disclosure can be used for treating a brain tissue damage. In more details, the APOSC of the present disclosure can improve the nerve function of individual having brain injury in the cell therapy. The transplanted APOSC can migrate to damaged parts of the brain and then repair nerve cells in the damaged parts. Therefore, the APOSC can treat a subject having the brain tissue damage, wherein the brain tissue damage can be a cerebral ischemic disease (such as a stroke) or a neural degenerative disease (such as an Alzheimer's disease, a Parkinson's disease and an epilepsy).

EXAMPLES

I. The Adult Pluripotent Olfactory Stem Cell (APOSC) of the Present Disclosure 1.1. Preparation of the APOSCs To prepare the APOSCs, the olfactory tissues of a mammal used in this example are human olfactory mucosa tissues or murine olfactory mucosa tissues. The human olfactory mucosa tissues (5 mm$^3$, 0.5 gm in weight, over the superior part of nasal cavity) are got from the nasal septum neighboring to the cribriform plate by an ethmoid forcep through the guidance of a nasal endoscope under general anesthesia. Protocols for sampling the human olfactory mucosa tissue are approved by the Institutional Review Board of China Medical University Hospital, Taichung, Taiwan. Written informed consents are obtained from all subjects. For the murine olfactory mucosa tissues preparation, Sprague-Dawley rats or mice, including C57BL/6J Narl, GFP-transgenic mice, Bmi-1$^{+/+}$ and Bmi-1$^{-/-}$, are used. Animals of 8-week or 11-week old are anesthetized, decapitated and their olfactory tissues (from superior turbinate) are isolated under a dissecting microscope.

Biopsy specimens of the human olfactory mucosa tissues are collected into in sterile boxes containing Hanks' balanced salt solution (Gibco/BRL) for primary culture within 24 hours. In the explant culture method, the human olfactory mucosa tissue is carefully dissected into small pieces under a dissecting microscope and placed in a phosphate-buffered solution at room temperature. The tissue explants are collected by centrifugation at 600 g for 10 minutes. The resulting pellet is resuspended in DMEM/F12 medium containing 2 μg/mL heparin (Sigma), 20 ng/mL fibroblast growth factor 2 (FGF-2, R&D Systems) and 20 ng/mL epidermal growth factor (EGF, R&D Systems) and 1% penicillin/streptomycin (P/S, 100 U/mL). The tissue explant is placed in a 25 cm$^2$ flat flask and incubated in 5% $CO_2$ at 37° C. The tissue explant is left undisturbed for 5-7 days to allow for migration of the cells from the explants. These primary adherent cells are the APOSCs isolated from the human olfactory mucosa tissue (human APOSCs). The preparation procedure of the APOSCs isolated from the murine olfactory mucosa tissue (mouse APOSCs) is the same as above, but the culture medium is further supplemented with 20 ng/ml EGF (invitrogen).

Pluripotent markers expressions of primary cultured APOSCs are analyzed by an immunocytochemistry analysis, a reverse transcription PCR (RT-PCR) and a flow cytometry analysis. The analyzed pluripotent markers include key transcription factors which are necessary for embryo sac development and cell surface glycosphingolipids presenting on undifferentiated human embryonic stem cells, wherein the key transcription factors include Nanog, Sox-2 and Oct-4, and the cell surface glycosphingolipid is SSEA-4 (stage-specific embryonic antigen 4).

Figure 1C:
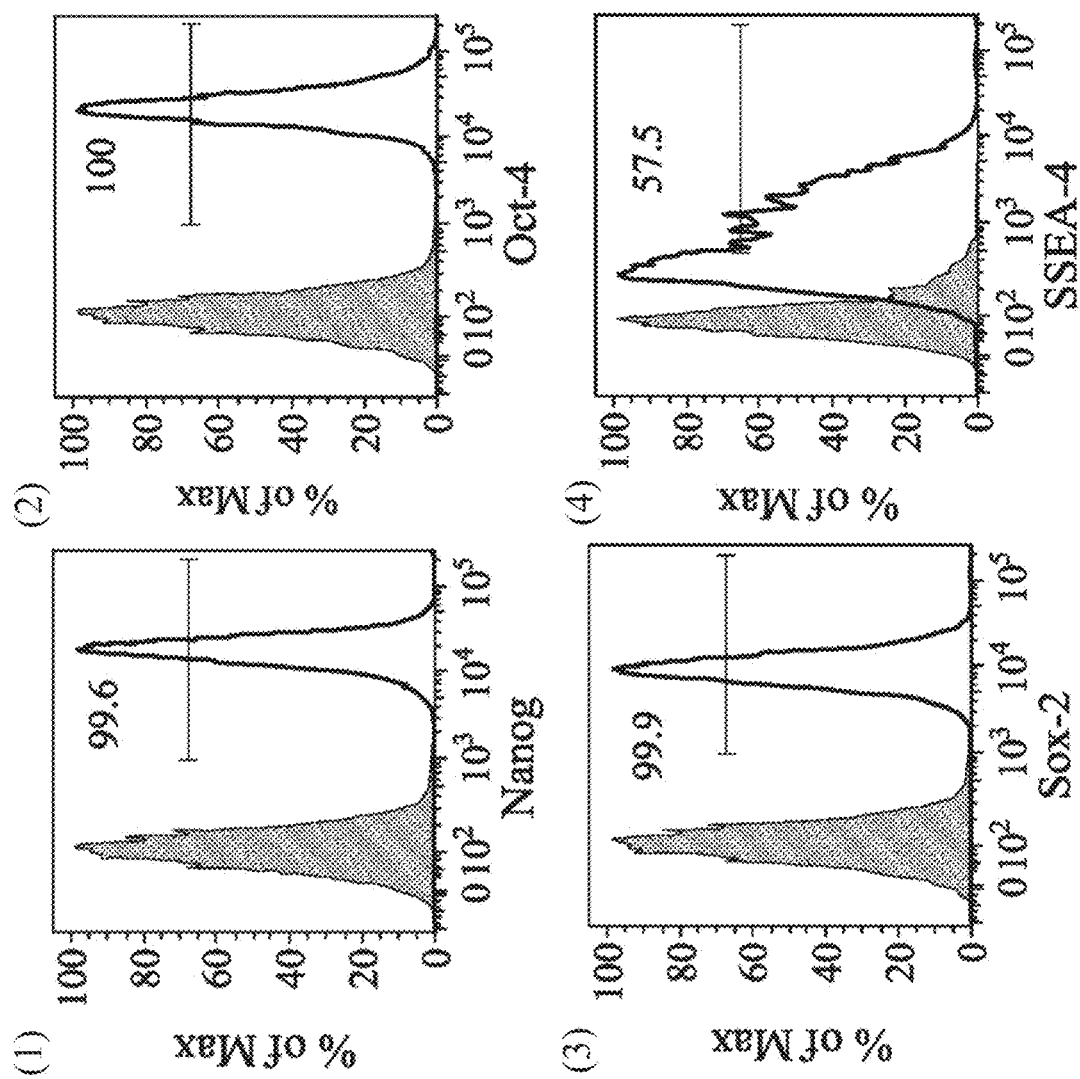
Figure 1B:
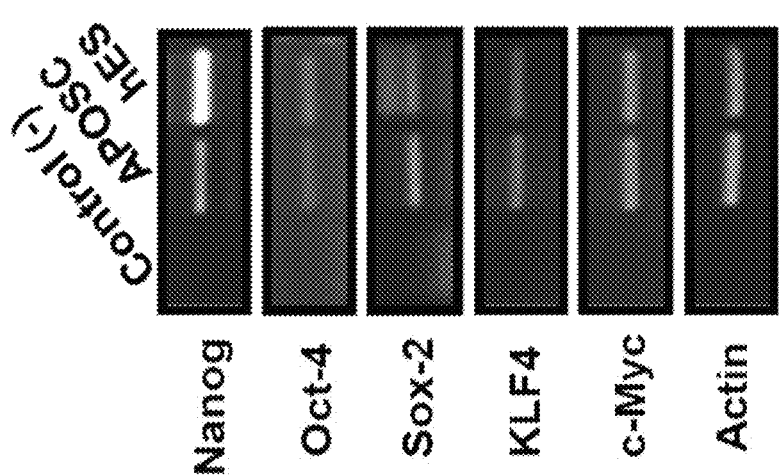

FIGS. 1A to 1C show analytical results of the human APOSCs. FIG. 1A shows the analytical results of the immunocytochemistry analysis, wherein blue fluorescence represents DAPI signal indicating nucleus, and green fluorescence of FIG. 1A-(1) to FIG. 1A-(4) represents signal of Nanog, Oct-4, Sox-2 and SSEA-4, respectively. FIG. 1B shows the analytical results of the RT-PCR, wherein control represents the group without adding template as the negative control, APOSC represents the group of the human APOSCs, and hES represents the group of the human embryonic stem cell as the positive control. FIG. 1C is the analytical results of flow cytometry analysis, wherein the APOSCs analyzed by the flow cytometry analysis are derived from 6 donors at various passages (p2-p14).

In FIG. 1A, the human APOSCs express the pluripotency markers such as Nanog, Oct-4, Sox-2 and SSEA-4, especially SSEA-4 expression on the cell surface of the APOSC represents that the APOSC is a primitive stage cell.

The immunocytochemistry analysis also confirms nuclear-expression of Nanog and Oct-4 in the APOSC derived from these 6 donors (data not shown). In FIG. 1B, the human APOSC express the pluripotency markers such as Nanog, Oct-4 and Sox-2. Moreover, the APOSC also express c-Myc and KLF-4 (Kruppel Like Factor 4), which contribute to the generation of induced pluripotent stem (iPS) cells. In FIG. 1C, the consistent result also indicates that the human APOSC express the pluripotency markers such as Nanog, Oct-4, Sox-2 and SSEA-4. The analytical results of the flow cytometry analysis show that 52.9±19.3% (n=6 donors) of these cell populations are positive for SSEA-4. In addition, 0.1 to 5% of the APOSCs are positive for SSEA-3, a more primitive-stage marker (data not shown). The analytical results above can demonstrate that inter donors-/or inter passages-derived APOSCs all express a consensus profile of pluripotency-related ESC markers.

Figures 1D, 1E:
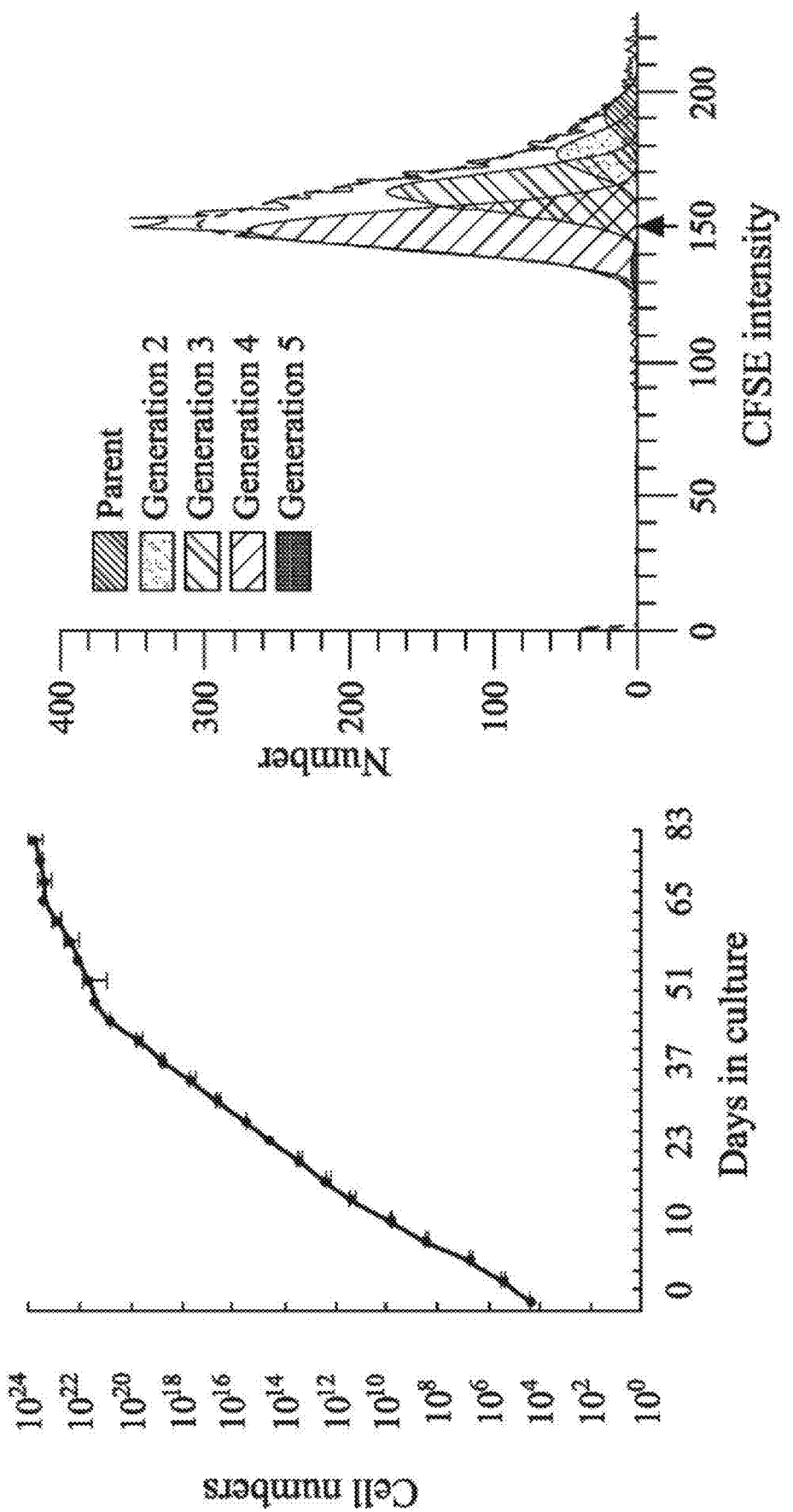
FIG. 1D is an exponential growth curve of the human APOSCs.
FIG. 1E shows an analytical result of a proliferation index (PI) measurement of the human APOSCs.

To analyze proliferation ability of in vitro cultivated APOSCs, long-term expansion of the APOSCs is achieved. FIG. 1D is an exponential growth curve of the human APOSCs. In FIG. 1D, the APOSCs proliferate exponentially for 48 days (17 passages), and grow slowly after 83 days (25 passages). The calculated doubling time of the APOSCs is 20.9±3.9 hours (donor 1, average of passages 3 to 17), or 25.3±6.7 (donor 2, average of passages 5 to 19) hours.

To monitor cell proliferation, the APOSCs are pulse labeled with 10 µM CFSE (carboxyfluorescein succinimidyl ester, Molecular probes). After 4 days of culture, the CFSE staining dilution profile (indicating cell proliferation) is evaluated by flow cytometry (Becton Dickinson). The data is calculated using MODFIT software (Verity Software House, Topsham, Me.) to obtain proliferation index (PI) of the APOSCs, wherein the higher calculated PI indicates the better cell proliferation ability. Because the fluorescence of the CSFE is precisely halved at each successive cell generation, the cell division of the APOSCs can be tracked by pulse labeling cells with CSFE for substantiating active growing phenotype of the APOSCs. FIG. 1E shows an analytical result of the PI measurement of the human APOSCs. During the 96 hours tracking period, 50.9% APOSCs had completed up to 3 divisions, and 32.7% APOSCs completed 2 cell divisions. It shows that the cell cycle kinetic of the APOSCs is equivalent to human ES, iPS (doubling time between 24 to 48 hours) and excels some adult multipotent stem cells (doubling times varying from 30 to 72 hours).

Figure 1F:
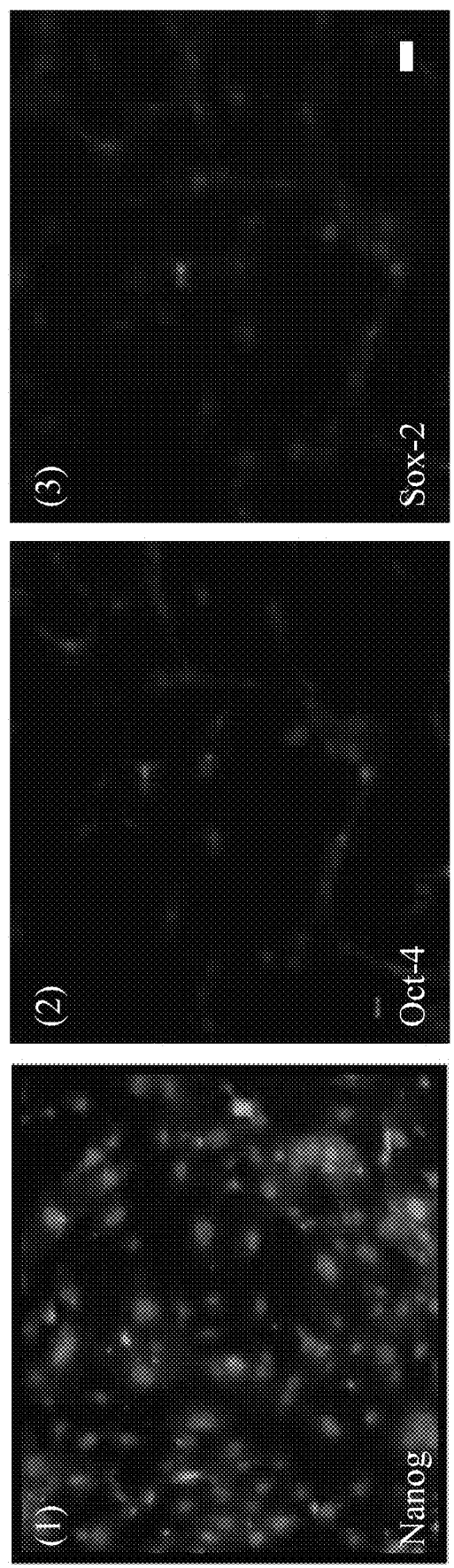
FIGS. 1F and 1G show analytical results of the pluripotent markers expressions of the adult pluripotent olfactory stem cells isolated from murine olfactory mucosa tissues (mouse APOSCs)
Figure 1G:
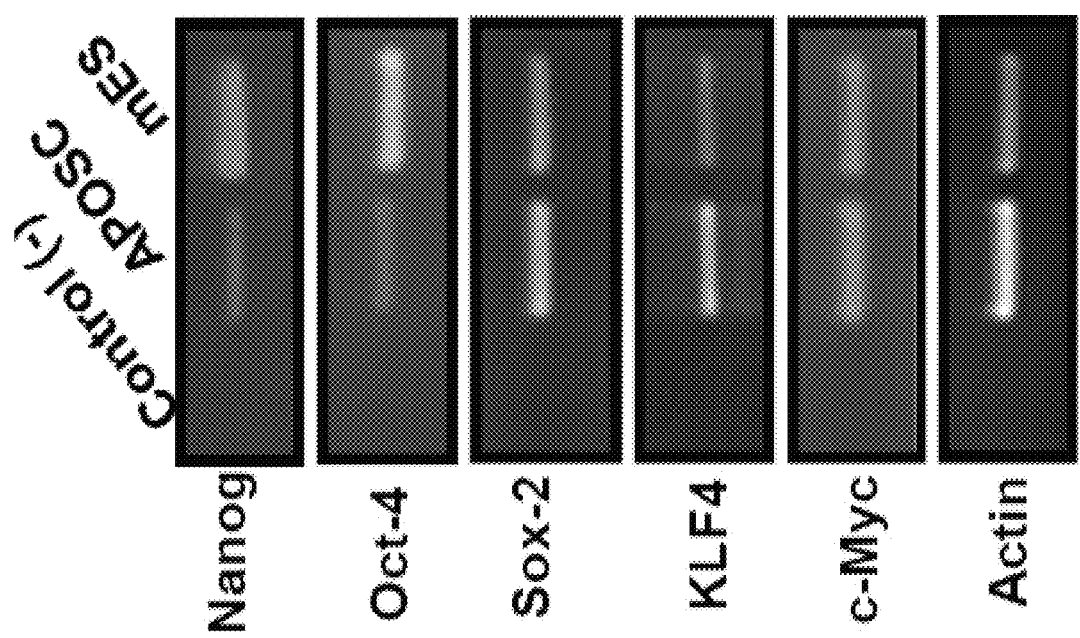

FIGS. 1F and 1G show analytical results of the pluripotent markers expressions of mouse APOSCs. FIG. 1F shows the analytical results of the immunocytochemistry analysis, wherein the blue fluorescence represents DAPI signal indicating nucleus, the green fluorescence of FIG. 1F-(1) and FIG. 1F-(3) represents signal of Nanog and Sox-2, respectively, and red fluorescence of FIG. 1F-(2) represents signal of Oct-4. FIG. 1G shows the analytical results of the RT-PCR, wherein control represents the group without adding template as the negative control, APOSC represents the group of the mouse APOSCs, and mES represents the group of the mouse embryonic stem cell as the positive control. In FIGS. 1F and 1G, the mouse APOSCs also express Nanog, Oct-4 and Sox-2 within nucleus, as well as KLF-4 and c-Myc. The doubling time of the mouse APOSCs is 24.6±2.0 hours.

1.2. Three-Dimensional Culture of the APOSCs

One of the distinct characteristic of stem cells is their ability to form spheres when subjected to a three-dimensional, natural niche-mimicking environment. Therefore, aside from adhesively growing, the APOSCs of the present disclosure are cultivated under a three-dimensional culture condition to examine whether they can maintain their stemness as spheres in this example.

The steps of three-dimensional culture are as follows. Sub-confluency APOSCs are trypsinized and resuspended as $7 \times 10^4$ cells per milliliter of sphere culture medium, consisting of DMEM/F12, 2% B27 supplement (Gibco), 20 ng/ml basic fibroblast growth factor (bFGF), 20 ng/ml EGF and 1% penicillin/streptomycin (100 U/ml). To avoid attachment of cells to the bottom of culture dishes, 15 mg/ml poly HEMA (Sigma, P3932) is coated on culture dishes before seeding the cell suspension. These primary sphere-forming cells arising from the APOSCs are termed 1st APOSC spheres. In order to detect proliferation potential of the APOSC spheres, the 1st APOSC spheres are further cultured in suspension culture medium containing Bromodeoxyuridine (BrdU) to label DNA.

Figure 2A:
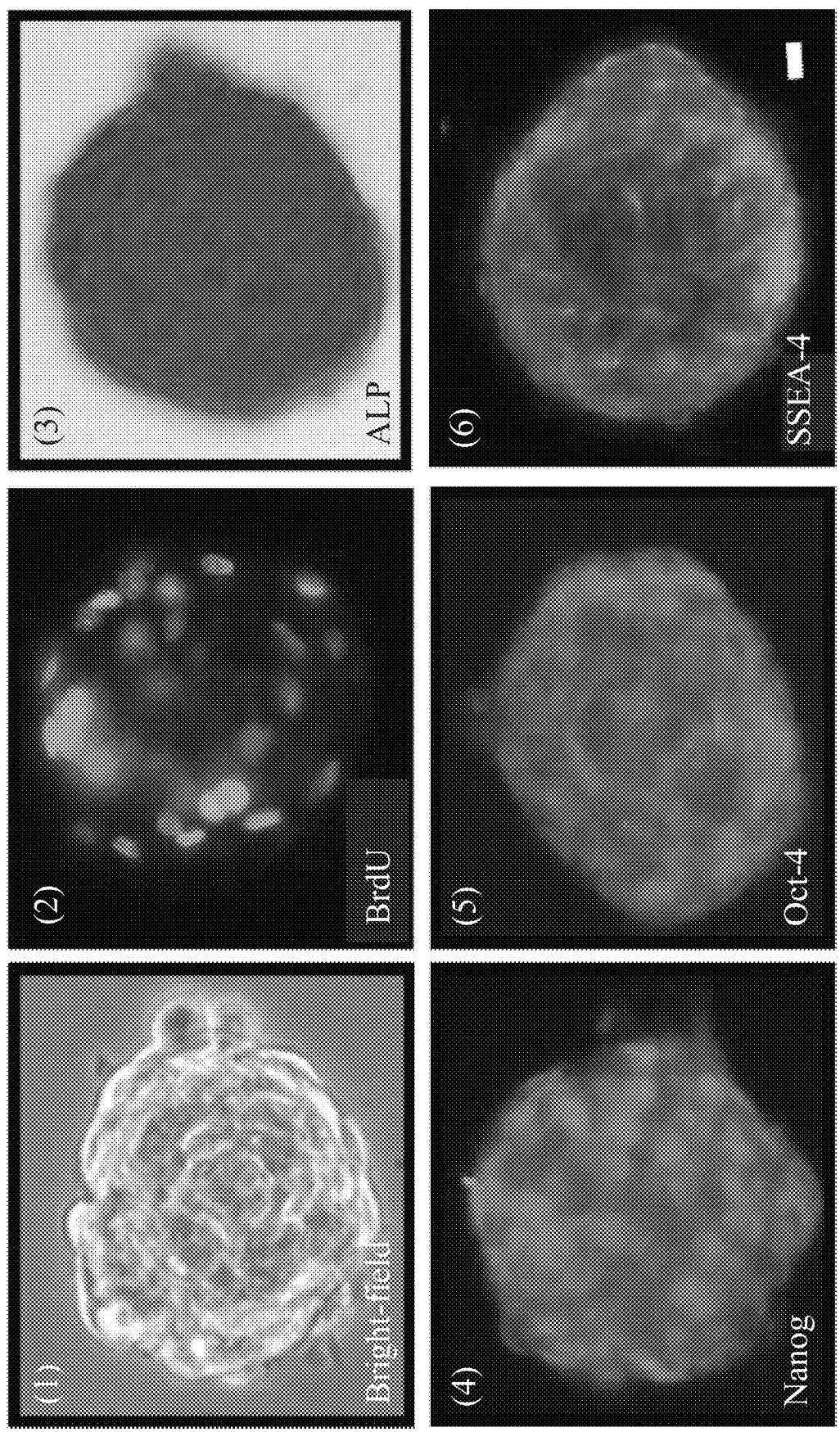
FIG. 2A shows analytical results of the pluripotent markers expressions of the human APOSCs after a three-dimensional culture.

FIG. 2A shows analytical results of the pluripotent markers expressions of the human APOSCs after a three-dimensional culture, wherein FIG. 2A-(1) is a micrograph under the bright-field, and FIG. 2A-(2) is a fluorescence micrograph of the APOSC sphere labeled with BrdU. In FIG. 2A, the human APOSCs effectively form compact floating spheres in three-dimensional cultures. The incorporation of BrdU in the 1st APOSC spheres demonstrates their persistent entry into S phase. The cell proliferation marker, Ki67, is also abundantly express in the 1st APOSC spheres (data not shown).

Sphere numbers over multiple passages represent stem cells self-renewal activity, whereas sphere size demonstrates cell proliferation. To evaluate the self-renewal capacity of the APOSC spheres, 3 days-cultured 1st APOSC spheres are trypsin-dissociated to single cells, cell number counted and re-plated in sphere culture medium. The subsequent spheres formed from trypsin-dissociated 1st spheres are termed 2nd APOSC spheres. For growth detection, the diameters of 2nd APOSC spheres are measured at day 2, 5 and 9 of cultures. After 2 days, 50% of the dissociated cells survive and the 2nd APOSC spheres are observed arisen in the three-dimensional culture. The diameter of the 2nd APOSC spheres that cultivated over 9 days is measured, demonstrating an increase of mean diameter of these spheres from 59 to 81 μm.

Please refer FIG. 2A again, FIG. 2A-(3) shows the analytical result of an alkaline phosphatase (ALP) staining by using Vector Red Alkaline Phosphatase Substrate Kit I, and FIGS. 2A-(4) to 2A-(6) show the analytical results of the immunocytochemistry analysis to label Nanog, Oct-4 and SSEA-4, respectively. In FIG. 2A, the APOSC spheres are positive for Nanog, Oct-4 and SSEA-4. Similar to the ESCs, the ALP activity is detected in the APOSC spheres.

Figure 2B:
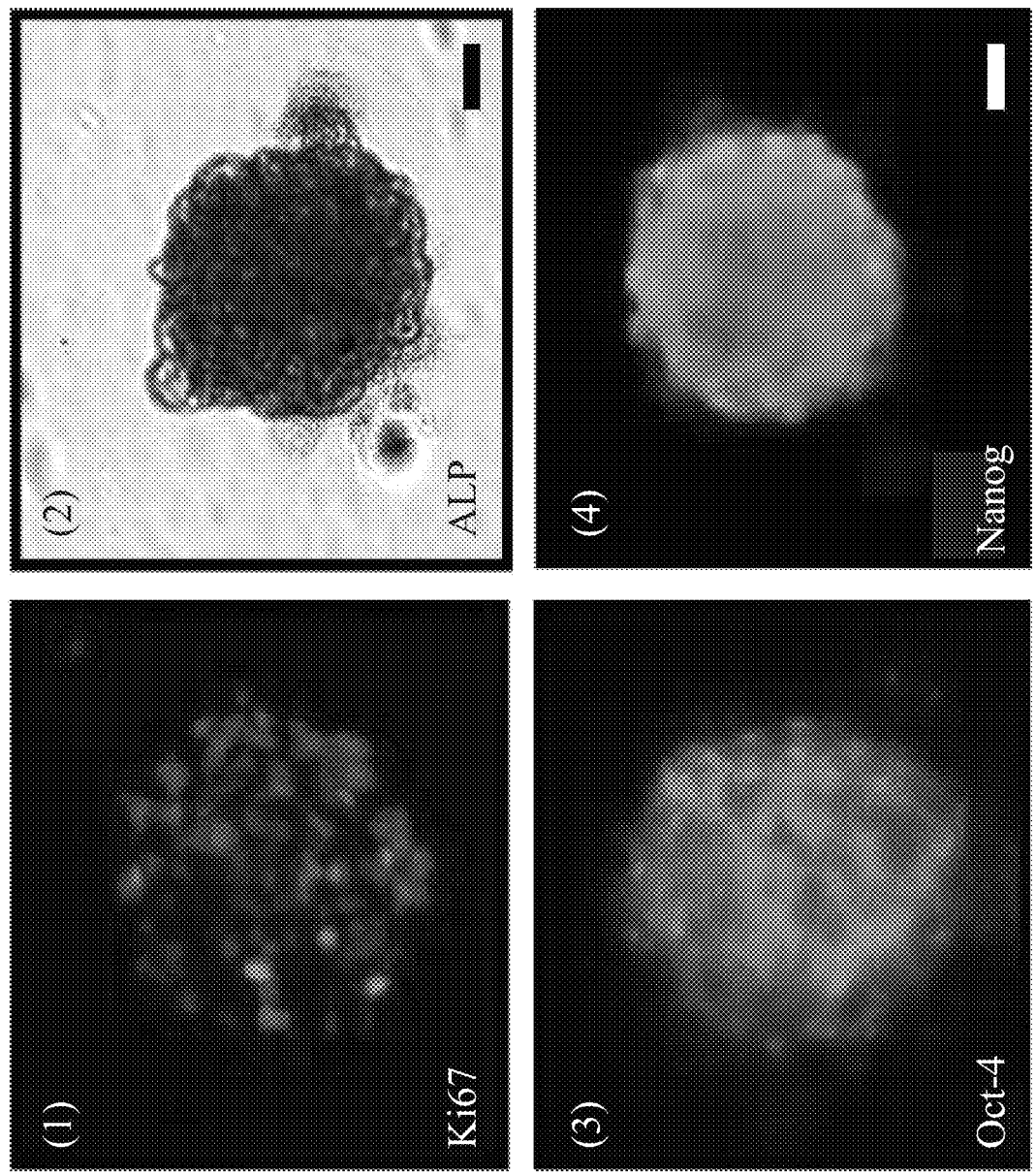
FIG. 2B shows analytical results of the pluripotent markers expressions of the mouse APOSCs after the three-dimensional culture.

FIG. 2B shows the analytical results of the pluripotent markers expressions of the mouse APOSCs after the three-dimensional culture, wherein FIG. 2B-(1) is the fluorescence micrograph of the APOSC sphere labeled with ki67, FIG. 2B-(2) shows the analytical result of the ALP staining, FIG. 2B-(3) shows the analytical result of the immunocytochemistry analysis for Oct-4, and FIG. 2B-(4) shows the analytical result of the immunocytochemistry analysis for Nanog. In FIG. 2B, the mouse APOSC spheres also express ki67, ALP, Oct-4 and Nanog. The foregoing results indicate that the expressions of pluripotent markers, self-renewal and alkaline phosphatase activity in the APOSC spheres of the present disclosure represent their ESC-mimicking characteristics.

1.3. Multipotent Differentiation Potential of the APOSCs In Vitro

The pluripotency in the APOSCs is further substantiated by demonstrating their three-germ layers-differentiation ability in vitro. To analyze the differentiation ability of the APOSCs, certain growth factors-based induction systems are used to guide the APOSCs to differentiate into ectoderm (neural cells), mesoderm (adipocytes, osteoblasts, chondrocytes and endothelial cells) or endoderm (hepatocytes). The cell morphology is observed under a microscope, and the cell type after differentiation is further confirmed by staining.

Figure 3A:
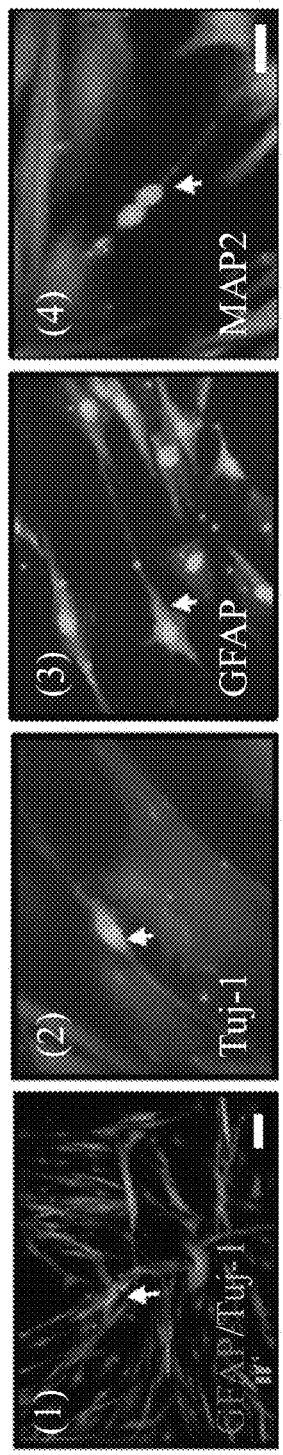
FIGS. 3A to 3E are analytical results showing induced differentiation of the adult pluripotent olfactory stem cells (APOSCs) into cell lineages of three-germ layers in vitro.

FIG. 3A shows micrographs of induced differentiation of the APOSCs into the neural cells of the ectoderm in vitro. The immunocytochemistry analysis is used to confirm whether the differentiated cells express mature nerve markers, wherein the mature nerve markers include Tuj-1 (Neuron-specific class III beta-tubulin), GFAP (glial fibrillary acidic protein) and MAP-2 (microtubule-associated protein 2). In FIG. 3A, the APOSCs cultured in neuronal differentiation medium are positive for the neuronal marker Tuj-1, GFAP and MAP2. These cells also exhibit neuronal morphologies, including multipolar morphology and branching (arrow) in FIG. 3A-(1), long bipolar thread-like morphology resembling developing olfactory receptor neuron (ORN) in FIG. 3A-(2), beaded axon-like structures (arrow) in FIG. 3A-(3) or webbed axon-like structures (arrow) in FIG. 3A-(4). These results prove that the cells after differentiation are indeed nerve cells.

Figure 3B:
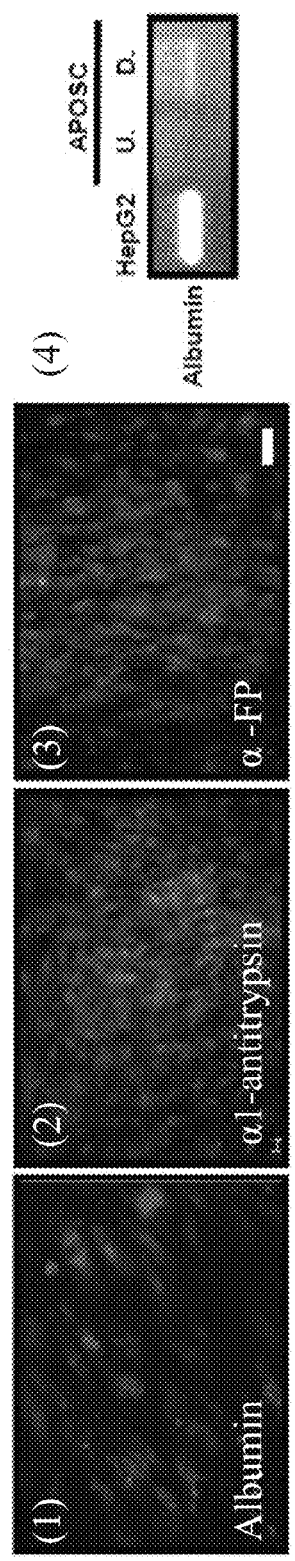
Figure 3C:
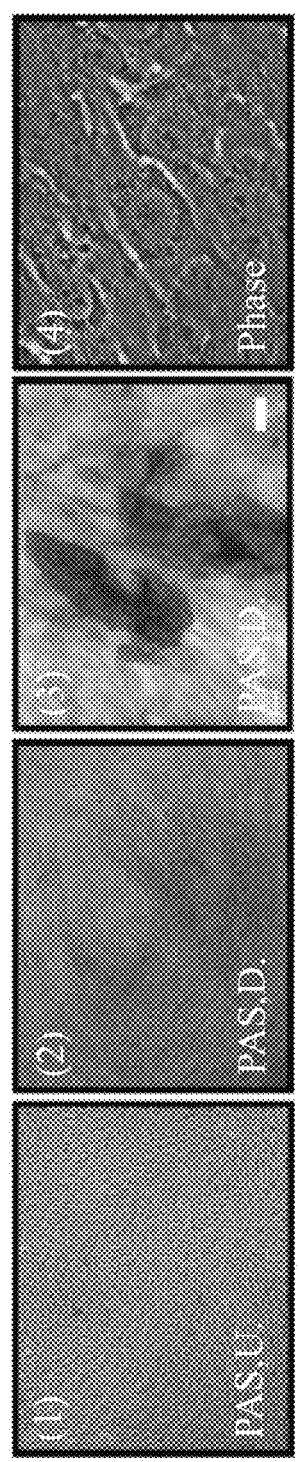

FIG. 3B shows analytical results of induced differentiation of the APOSCs into the hepatocytes of the endoderm in vitro. FIGS. 3B-(1) to 3B-(3) are the analytical results of the immunocytochemistry analysis for detecting whether the differentiated APOSCs express hepatocyte-specific genes, including albumin, α-1-anti-trypsin and α-fetoprotein (α-FP). FIG. 3B-(4) shows the analytical results of the RT-PCR for confirming albumin expression in differentiated APOSCs, wherein human liver carcinoma cell line (HepG2) is served as positive control, U represents undifferentiated APOSCs, and D represents differentiated APOSCs. In FIG. 3B, hepatocyte induction produced cells positive for hepatocyte-specific genes, including albumin, α1-antitrypsin and human α-feto-protein. To test for hepatocellular metabolic functions, polyglycans are stained by a periodic acid Schiff (PAS) assay, which indicates whether glycogen storage within the cytoplasm of the differentiated APOSCs. FIG. 3C shows micrographs of the APOSCs stained with the PAS assay, wherein U represents undifferentiated APOSCs, and D represents differentiated APOSCs. In FIG. 3C-(1), there is no glycogen storage within the undifferentiated APOSCs. But in FIGS. 3C-(2) and 3C-(3), there are glycogen storage within the cytoplasm of the differentiated APOSCs, wherein FIG. 3C-(2) is 40× power image and FIG. 3C-(3) is 400× power image. Taken together, the APOSC can be induced to differentiate into functional hepatocytes.

Figure 3D:
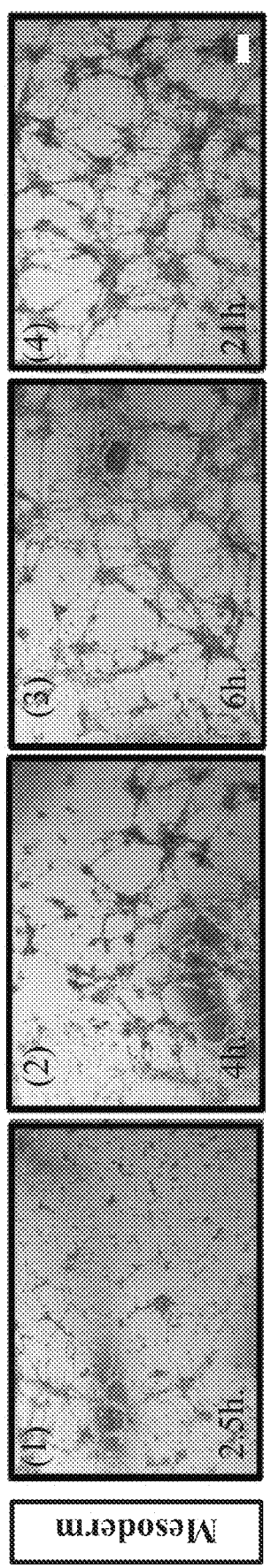

FIG. 3D shows micrographs of induced differentiation of the APOSCs into the endothelial cells in tube formation assay. To induce the APOSCs toward the endothelial cells, the APOSCs are grown in DMEM medium supplemented with vascular endothelial growth factor (VEGF), bFGF and heparin. After 8-10 days, the cells are analyzed by in vitro tube formation assay and observed their cell morphology in the bright field to confirm whether the APOSCs differentiate into the endothelial cells. As shown in FIG. 3D, in the tube formation assay, the APOSCs initially attach, migrate toward each other within 2-4 hours and then form capillary-like tubes, which mature by around 6 hours. After 21 hours, the tubes detached from the matrix and broke apart. Such tube formation kinetic is as typical as that behave by the endothelial cells.

Figure 3E:
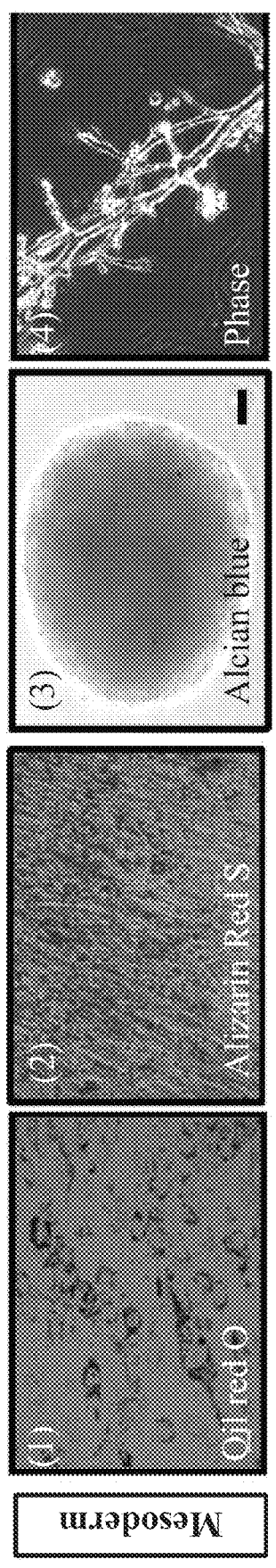

FIG. 3E shows micrographs of induced differentiation of the APOSCs into the adipocytes, the osteoblasts, the chondrocytes and the endothelial cells of the mesoderm in vitro. In FIG. 3E-(1), adipogenic differentiation of the APOSCs can be identified via Oil Red O staining, as an indicator for intracellular lipid accumulation. In FIG. 3E-(2), osteogenesis in the APOSCs is detected via Alizarin Red S staining to show calcium mineralization. In FIG. 3E-(3), chondrogenesis is detected via Alcian Blue staining, the indication of proteoglycans synthesized by differentiated-APOSCs. In FIG. 3E-(4), the APOSCs are grown in DMEM medium without angiogenic factors, and then observed their cell morphology in the bright field. As shown in FIG. 3E, the APOSCs can differentiate into the adipocytes, the osteoblasts and the chondrocytes, and form capillary-like tube structures. Without beforehand VEGF-induction, the APOSCs can also form tubes with a lumen in tube formation assay, although with a delayed kinetic (tube-growing begin at 48 hours). It suggests that the APOSCs not only can be directed by exogenously provided tissue-specific growth factors, they possibly have potential to differentiate spontaneously into three germ layers, just like the ESCs.

Figure 3F:
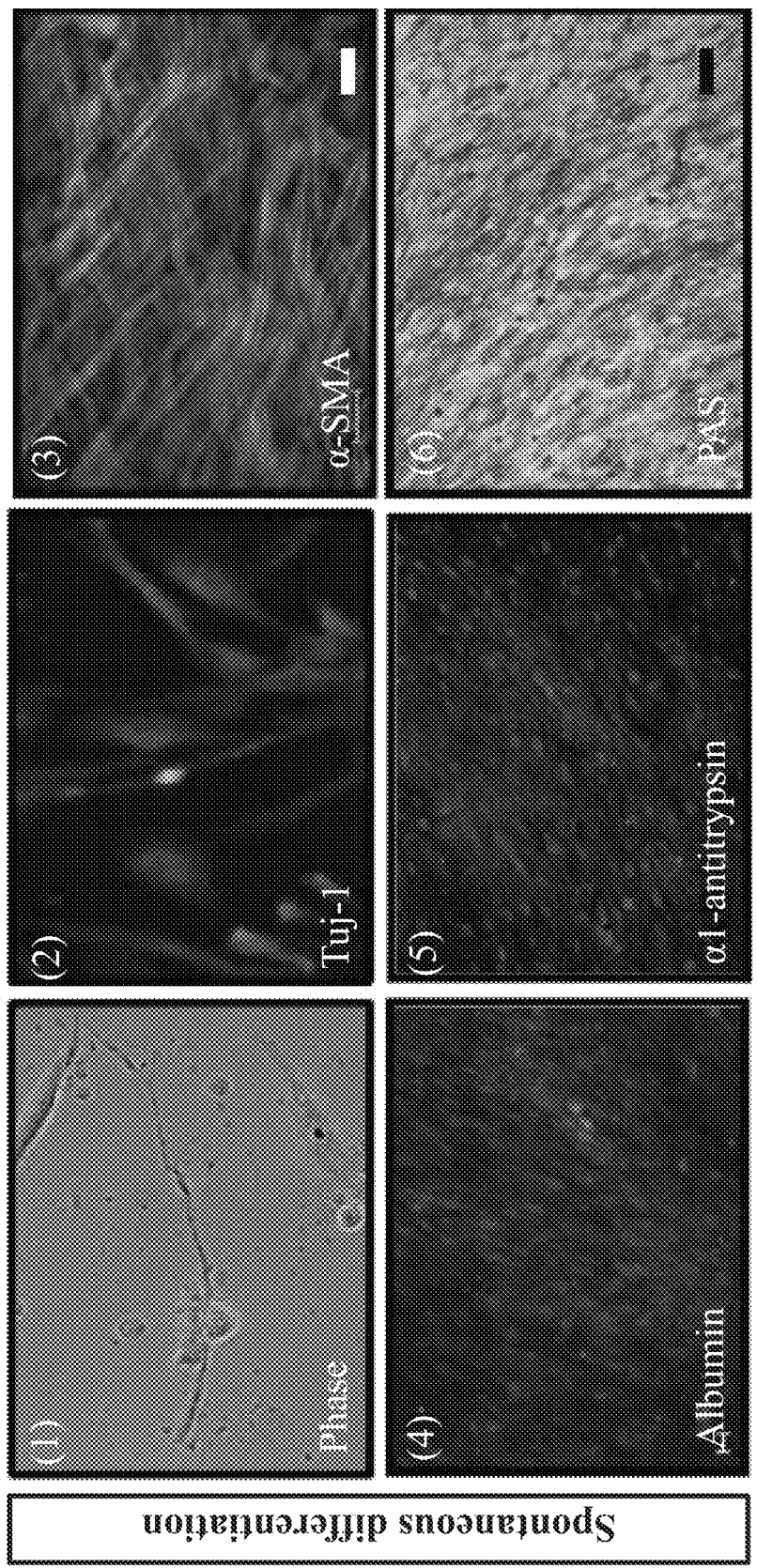
FIG. 3F shows micrographs of spontaneous differentiation of the APOSCs into cell lineages of three-germ layers in vitro.
Figure 3G:
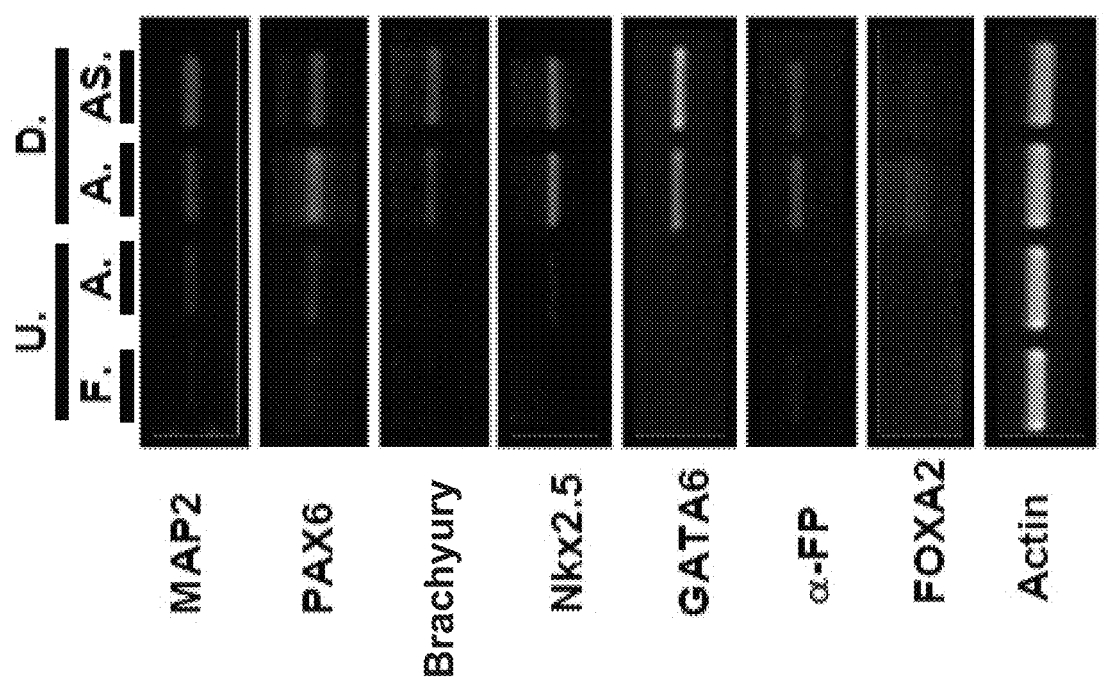
FIG. 3G shows analytical results of three-germ layer markers expressions of the APOSCs after the spontaneous differentiation.

Therefore, we next test whether the APOSCs can spontaneously differentiate into three germ layers-derived cells without any growth factors direction in this example. The APOSCs or the 1st APOSC spheres are transferred onto gelatin-coated dishes for 15 days of culture, and then the cells are analyzed by the staining and the RT-PCR to confirm whether they are differentiated into the cell lineages of three-germ layers. Please refer to FIGS. 3F and 3G, FIG. 3F are micrographs showing spontaneous differentiation of the APOSCs into cell lineages of three-germ layers in vitro, and FIG. 3G shows analytical results of three-germ layer markers expressions of the APOSCs after the spontaneous differentiation. In FIG. 3F-(1), neuron-like cells are observed among the spontaneously differentiated population. In FIG.

3F-(2), the spontaneously differentiated cells are positive for the Tuj-1 (the ectodermic marker). In FIG. 3F-(3), the spontaneously differentiated cells are positive for α-smooth muscle actin (α-SMA; a mesodermic marker). In FIGS. 3F-(4) and 3F-(5), the spontaneously differentiated cells are positive for albumin and α1-antitrypsin (endodermic markers). In FIG. 3F-(6), the PAS assay shows the glycogen deposition in the spontaneously differentiated cells (indicating endodermic hepatocytes). In FIG. 3G, RT-PCR of gelatin-grown APOSCs/or 1st APOSC spheres confirm that these cells increasingly expressed ectodermic makers MAP2 and PAX6, mesodermic markers Brachyury and Nkx2.5, as well as endodermic markers GATA6, α-FP and FOXA2. These results prove again that the APOSCs of the present disclosure can differentiate spontaneously into the cell lineages of three-germ layers.

1.4. In Vivo Differentiation of the APOSCs

Furthermore, we test the in vivo-differentiation ability of the APOSCs by transplanting the human APOSCs into stroke mice in this example. Then we perform immunohistochemistry analysis to determine whether the human APOSCs can differentiate into the neurons, glial cells or the endothelial cells in cerebral ischemia area of the stroke mice brain.

An ischemia-reperfusion model is used to simulate transient focal cerebral ischemia in the mice. Test animals are adult male C57BL/6 mice weighing 25-30 g. The mice are intraperitoneally injected with chloral hydrate (0.4 g/kg) for anesthesia. The ischemia-reperfusion model is induced by ligations of bilateral common carotid arteries (CCAs) and a right middle cerebral artery (MCA). Cortical blood flow (CBF) is measured continuously with a laser Doppler flowmeter (PF-5010, Periflux system) in anesthetized animals. After 120 min ischemia, the suture on the MCA and the arterial clips on CCAs are removed to allow reperfusion. During anesthesia, core body temperature of the anesthetized animal is monitored with a thermistor probe and maintained at 37° C. using a heating pad. After recovery, body temperature of anesthetized animal is maintained at 37° C. with a heat lamp.

Prior to cells transplantation, the human APOSCs are first transduced with a lentivirus encoding the Luc gene to obtain the luciferase-labeled human APOSCs (hAPOSC-Luc). For intracerebral cell transplantation, the stroke mice under cerebral ischemia are injected stereotaxically with $10^6$ cells of the hAPOSC-Luc into three cortical areas, 3.5 mm below the dura. At 4 weeks, the mice are sacrificed and their brain tissues are subjected to the immunocytochemistry analysis for detecting the neuron marker MAP2, the glial cell marker GFAP and endothelial cell markers, such as Von Willebrand factor (vWF) and laminin to confirm whether the transplanted hAPOSC-Luc are differentiated into the neurons, the glial cells or the endothelial cells.

Figure 4A:
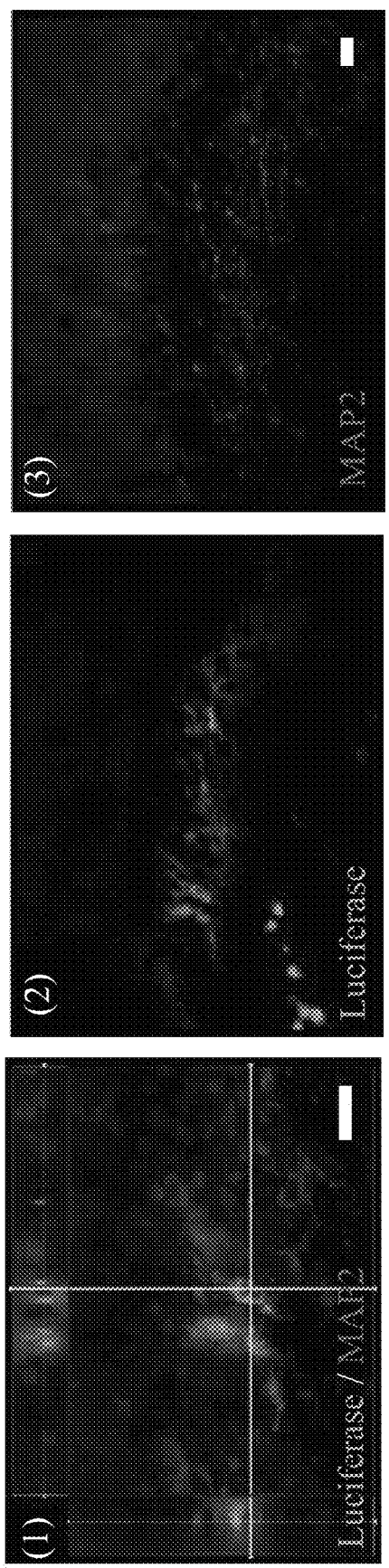
FIGS. 4A to 4E are micrographs showing in vivo differentiation of the human APOSCs into cell lineages of three-germ layers in mice.
Figure 4B:
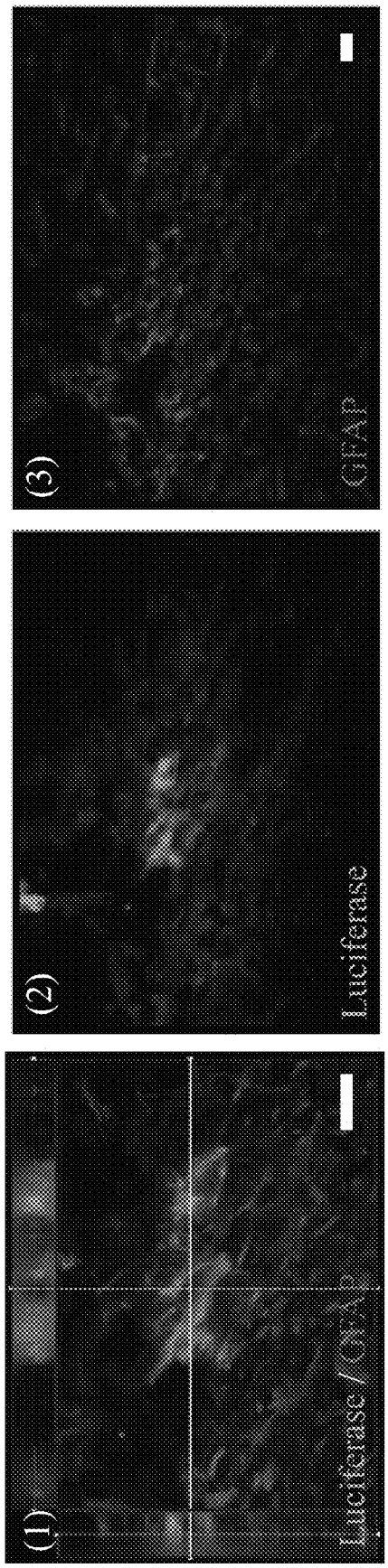
Figure 4C:
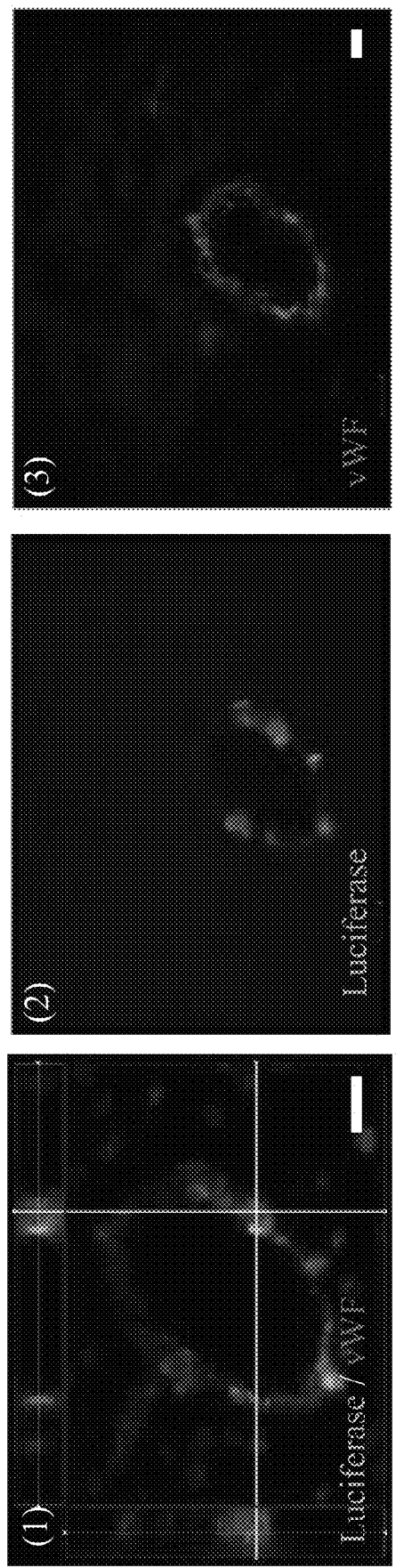
Figure 4D:
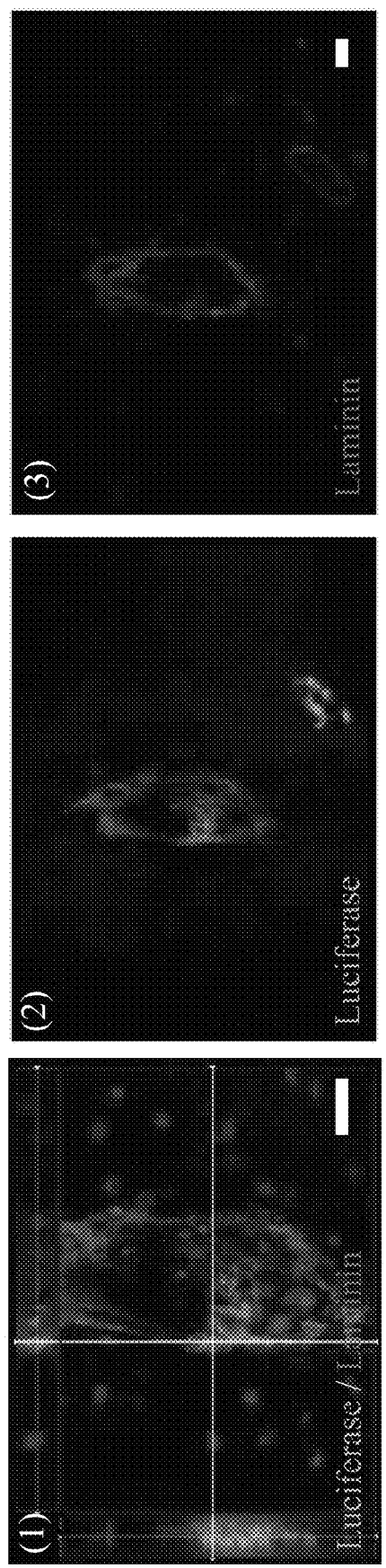

FIGS. 4A and 4B are micrographs showing that the human APOSCs are in vivo differentiated into the neurons and the glial cells in the mice. FIGS. 4C and 4D are micrographs showing that the human APOSCs are in vivo differentiated into the endothelial cells in the mice. In FIGS. 4A and 4B, exogenous transplanted hAPOSC-Luc engraft into the penumbra area, lateral ventricle (LV) and hippocampal dentate gyrus (DG) of the ischemic hemisphere. Immunofluorescent colocalization results show that some luciferase-labeled cells co-expressing MAP2 at DG or GFAP in penumbra area. In FIGS. 4C and 4D, the cells around the lumen of blood vessels co-express luciferase with endothelial cell markers, vWF or laminin.

Figure 4E:
Figure 5A:
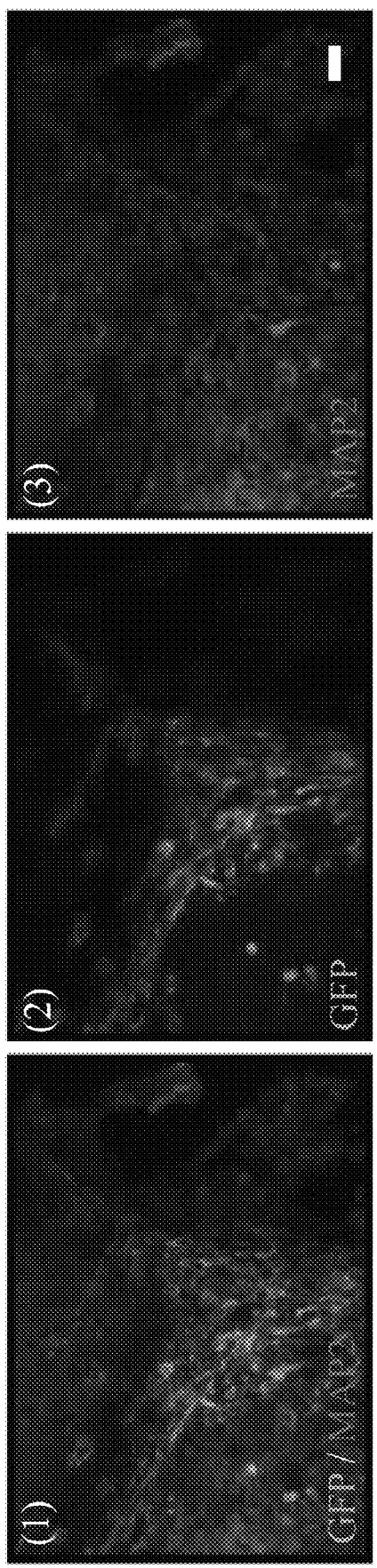
FIGS. 5A to 5D are micrographs showing in vivo differentiation of the mouse APOSCs into cell lineages of three-germ layers in mice.
Figure 5B:
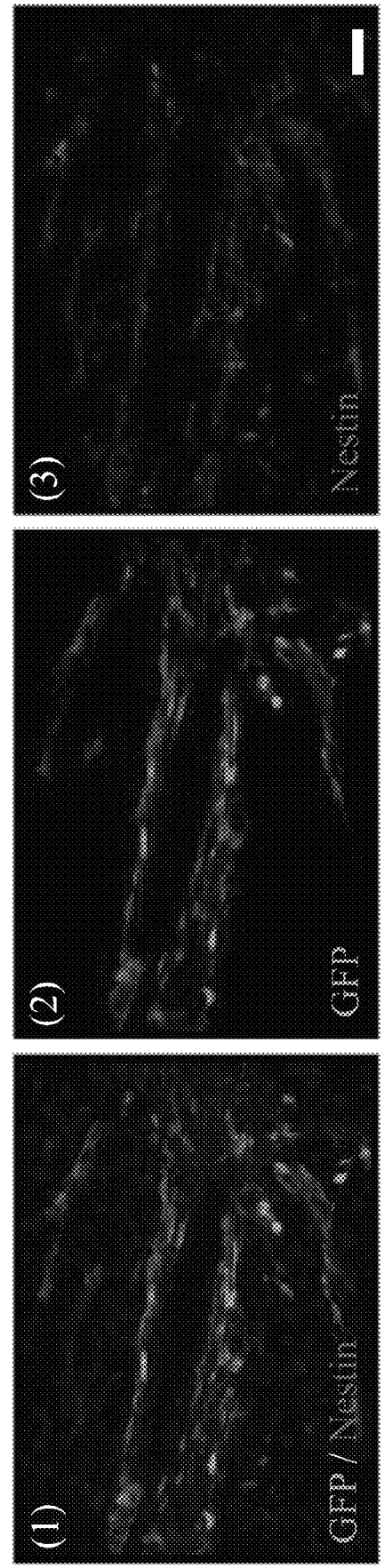
Figure 5C:
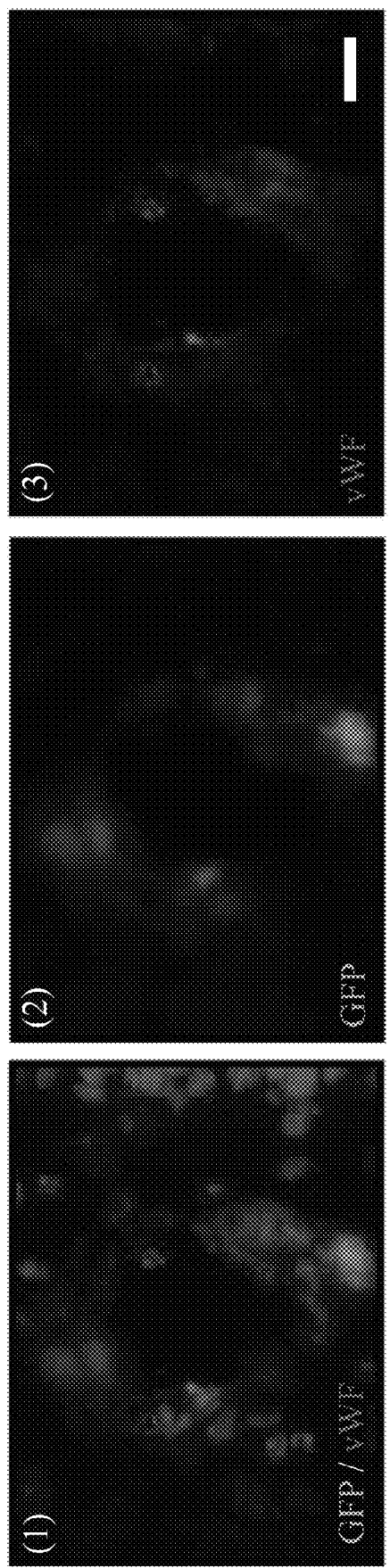
Figure 5D:
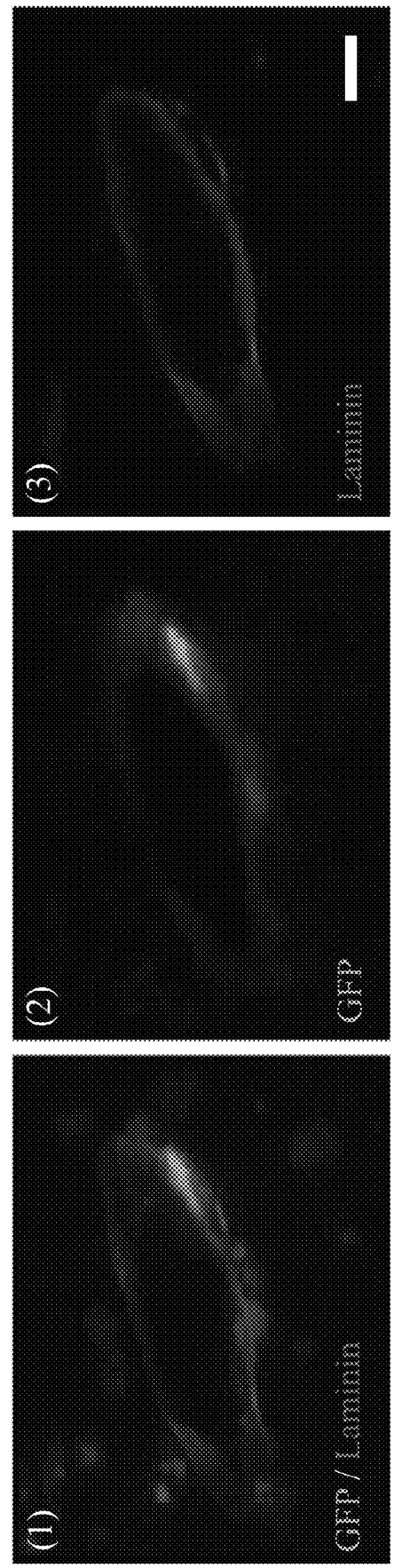

In order to further confirm that the APOSCs of the present disclosure can differentiate into the cell linages of the endoderm in vivo, $10^6$ cells of hAPOSC-Luc are transcutaneously injected into the liver of neonatal (day 2) mice. At 6 weeks, the mice are sacrificed and their liver tissues are subjected to immunocytochemistry analysis for detecting albumin synthesized by the hepatocytes to confirm whether the transplanted hAPOSC-Luc are differentiated into the liver cells. FIG. 4E shows micrographs that the human APOSCs are in vivo differentiated into the liver cells in the mice. In FIG. 4E, a few of hepatocytes co-expressing luciferase and human albumin can be detected over mice livers. These data demonstrated that the APOSCs can differentiate into ectodermal (neurons, glial cells), mesodermal (endothelial cells) and endodermal (hepatocyte) lineage cells in vivo.

FIGS. 5A to 5D are micrographs showing in vivo differentiation of the mouse APOSCs into cell lineages of three-germ layers in mice. The mouse APOSCs are derived from transgenic GFP-mice (mAPOSC-GFP), so they are labeled with green fluorescence. Other test steps are as the same as above and not repeat again here. In FIGS. 5A to 5D, the transplanted mAPOSC-GFP also migrate to the penumbra area, and differentiated into the neurons (MAP2$^+$ and Nestin$^+$) or the endothelial cells (vWF$^+$ and laminin$^+$).

1.5. The APOSC is Derived from Basal Layer of Adult Human and Murine Olfactory Epithelium The data of aforementioned examples demonstrate that the APOSCs express a plurality of specific pluripotent markers. Next, we demonstrate the in vivo distribution of the APOSCs in this example. As the APOSCs express a distinctive panel of pluripotency-markers, these markers might be used to identify the niche of endogenous APOSCs in the olfactory mucosa tissues.

FIG. 6A-(1) is a schematic diagram of cell types in human olfactory mucosa tissue, wherein OE represents olfactory mucosa, BM represents basal membrane, LP represents lamina propria, GBC represents globose basal cell, and HBC represents horizontal basal cell. In FIG. 6A, the HBC and the GBC remain in the human olfactory mucosa biopsy, but other cell types are lost during the sampling process. The HBC reside directly adjacent to the BM, which is indicated by the dotted line, and the LP is beneath the olfactory mucosa tissues. FIGS. 6A-(2) to 6A-(7) show in vivo distribution analytical results of the human APOSCs. The human olfactory mucosa tissue is labeled with Nanog, Sox-2, Oct-4 and SSEA-4, the APOSCs expressed markers, as well as HBC marker K14 (cytokeratin 14) by the immunocytochemistry analysis. In FIGS. 6A-(2) to 6A-(5), Nanog (green fluorescence in the nucleus), Sox-2 (green fluorescence in the nucleus), Oct-4 (green fluorescence in nucleolus and cytoplasm) and SSEA-4 (green fluorescence on the cell membrane) are co-expressed with K14 (red fluorescence in cytoplasm) in the human olfactory mucosa tissue, showing that the cells expressed Nanog, Sox-2, Oct-4 and SSEA-4 are distributed in the basal layer of the olfactory mucosa tissue. In FIGS. 6A-(6) and 6A-(7), the cells distributed in the basal layer co-express either SSEA-4 and Nanog or Sox-2 and Nanog.

Note that in the human olfactory mucosa tissue, both the HBC and the GBC express K14 and have round cell bodies, unlike in murine olfactory mucosa tissue that the HBC solely express K14 and display flat/horizontal morphology.

To precisely identify the APOSC niche, we further examine murine complete olfactory mucosa, which is obtained from rat superior turbinate tissue. FIG. 6B-(1) is a schematic diagram of cell types in the murine olfactory mucosa tissue, wherein OE represents the olfactory mucosa, BM represents the basal membrane, LP represents the lamina propria, GBC represents the globose basal cell, HBC represents the horizontal basal cell, ORN represents olfactory receptor neurons and Sus represents sustentacular cells. FIGS. 6B-(2) to 6B-(4) show in vivo distribution analytical results of the mouse APOSCs. The murine olfactory mucosa tissue is labeled with Nanog, Sox-2 and Oct-4, the APOSCs expressed markers, as well as the HBC marker K14 by the immunocytochemistry analysis. In FIGS. 6B-(2) to 6B-(4), Nanog (red fluorescence), Sox-2 (red fluorescence) and Oct-4 (red fluorescence) are co-expressed with K14 (green fluorescence in cytoplasm) in the murine olfactory mucosa tissue, showing that the cells expressed Nanog, Sox-2 and Oct-4 are distributed in the basal layer of the olfactory mucosa tissue.

Figure 6C:
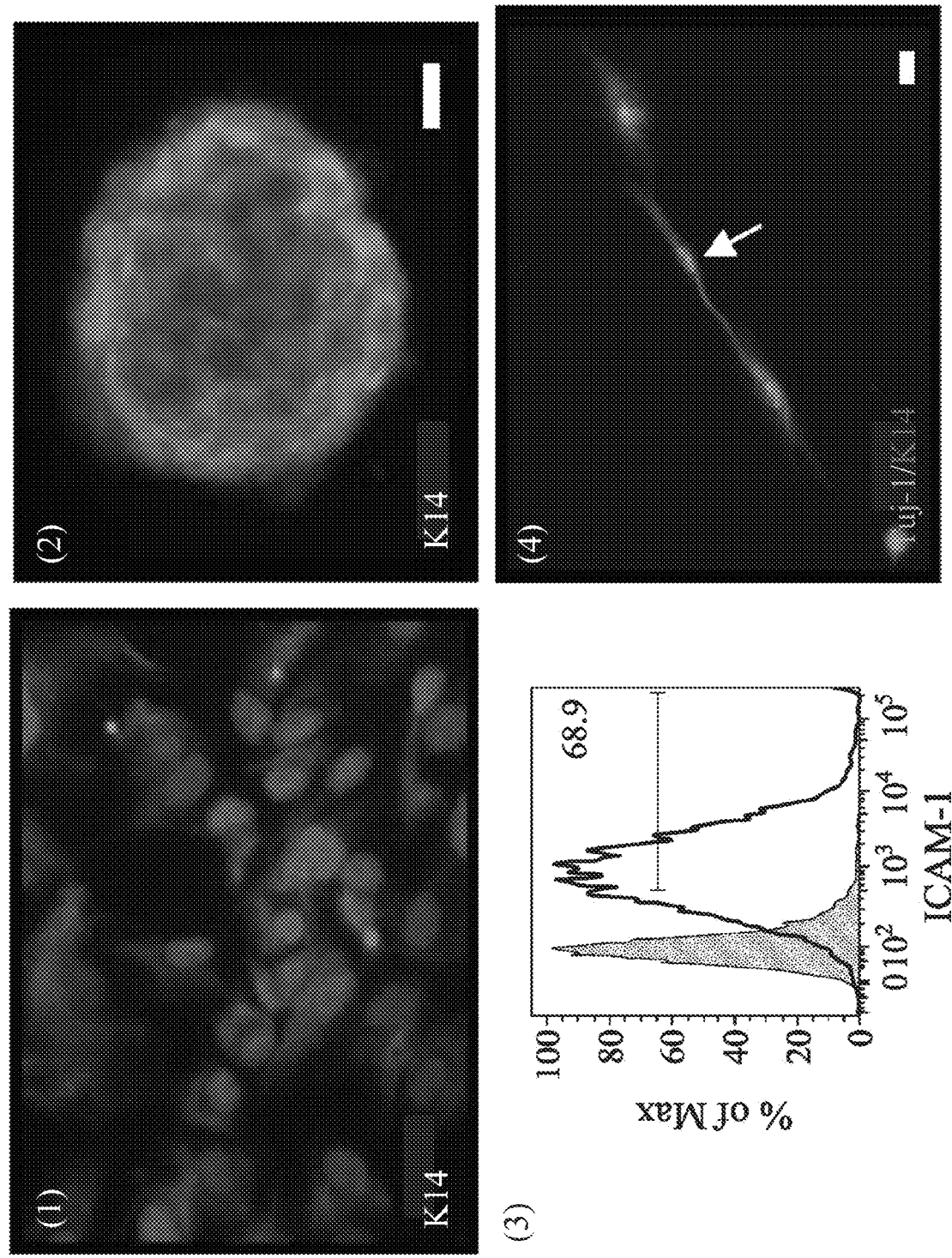
FIG. 6C shows analytical results of horizontal basal cell (HBC) markers expressions of in vitro cultured APOSCs.

FIG. 6C shows analytical results of HBC markers expressions of in vitro cultured APOSCs, wherein the analyzed cells include in vitro cultured APOSCs and APOSC spheres, and the HBC markers include K14 and ICAM-1 (intercellular adhesion molecule 1). In FIGS. 6C-(1) to 6C-(3), the in vitro cultured APOSCs and APOSC spheres also express K14 and ICAM-1. Additionally, in FIG. 6C-(4), upon induced-differentiation toward neurons, the APOSCs lose expression of K14 while gain expression of Tuj-1. Therefore, these results indicate that the human APOSCs and the mouse APOSCs reside within the adult basal layer of the olfactory mucosa tissue.

1.6. Bmi-1 is Essential for APOSC Self-Renewal

Figure 7A:
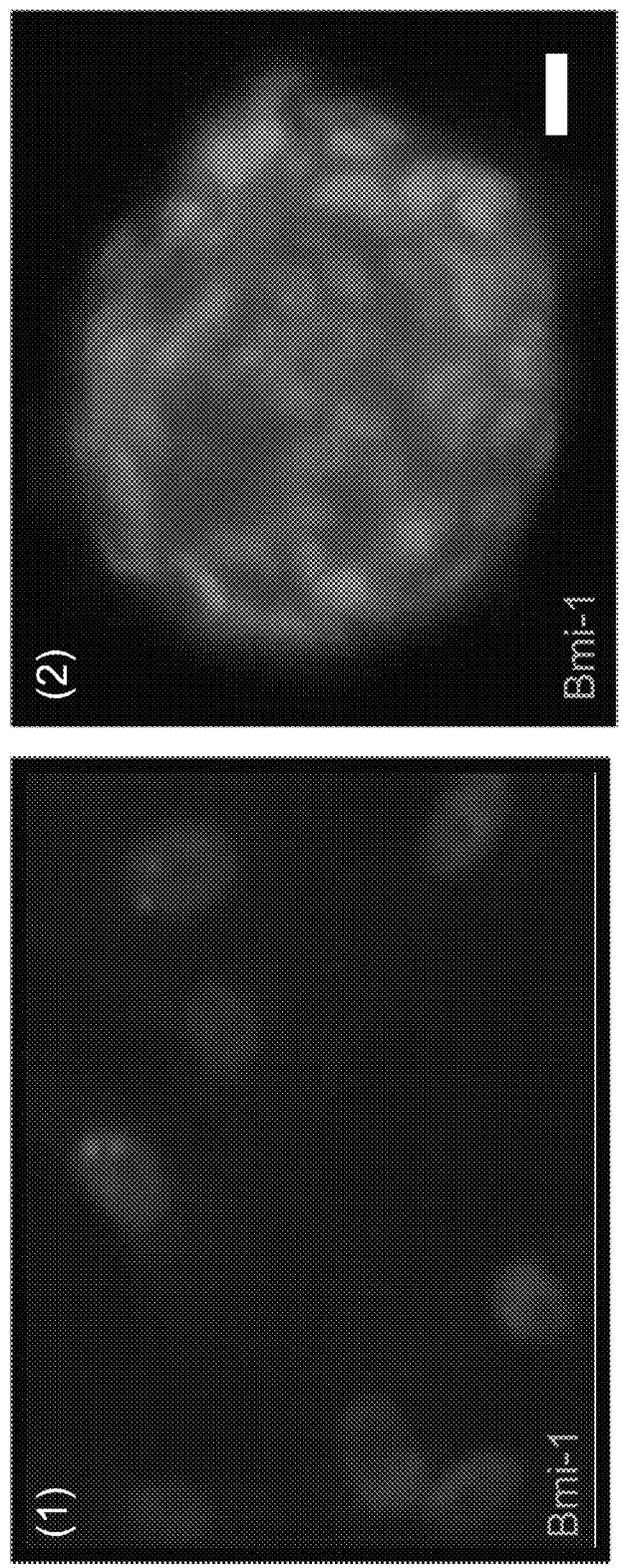
FIG. 7A shows analytical results of expressions of Bmi-1 of in vitro cultured APOSCs.
Figure 7B:
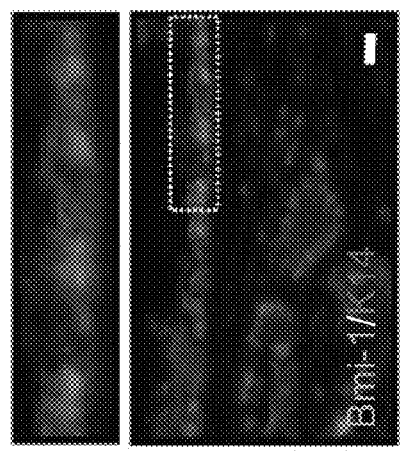
FIG. 7B shows analytical results of the expressions of the Bmi-1 of the human APOSCs.
Figure 7C:
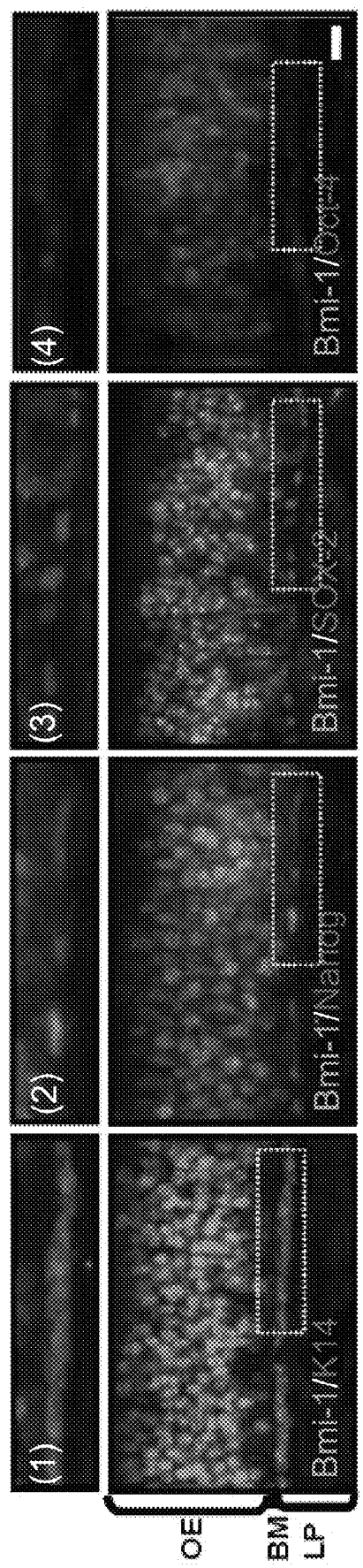
FIG. 7C shows analytical results of the Bmi-1 expressions of the mouse APOSCs.

Furthermore, we explore the role of Bmi-1 as a putative molecular mechanism that maintained the APOSCs. FIG. 7A shows analytical results of Bmi-1 expressions of in vitro cultured APOSCs, wherein the green fluorescence represents signal of Bmi-1, and the blue fluorescence represents DAPI signal indicating nucleus. FIG. 7B shows analytical results of the Bmi-1 expressions of the human APOSCs. FIG. 7C shows analytical results of the Bmi-1 expressions of the murine APOSCs. The APOSCs are cultivated under the adherent culture condition in FIG. 7A-(1), and the APOSCs are cultivated under the three-dimensional culture condition in FIG. 7A-(2). The results in FIGS. 7A-(1) and 7A-(2) show that in vitro cultured APOSCs and APOSC spheres both express Bmi-1. In FIGS. 7B and 7C, whether in the human olfactory mucosa tissues or the murine olfactory mucosa tissues, Bmi-1 is expressed evidently in the nuclei of the APOSCs, which co-expresses with pluripotency-related markers Nanog, Sox-2, Oct-4 or HBC markers K14. Besides, in FIG. 7C-(1), abundant Bmi-1 accumulate as polycomb-group bodies in the ORN, consistent with previous reports that Bmi-1 is expressed in post-mitotic neurons of the mature brain and ocular tissues. In FIGS. 7B and 7C, aside from the HBC and the ORN, just minimal level of Bmi-1 is observed in the GBC and the sustentacular cells (Sus). In conclusion, the APOSCs not only robustly express the ESC markers, but also express the adult stem cell gene, Bmi-1.

Figure 8A:
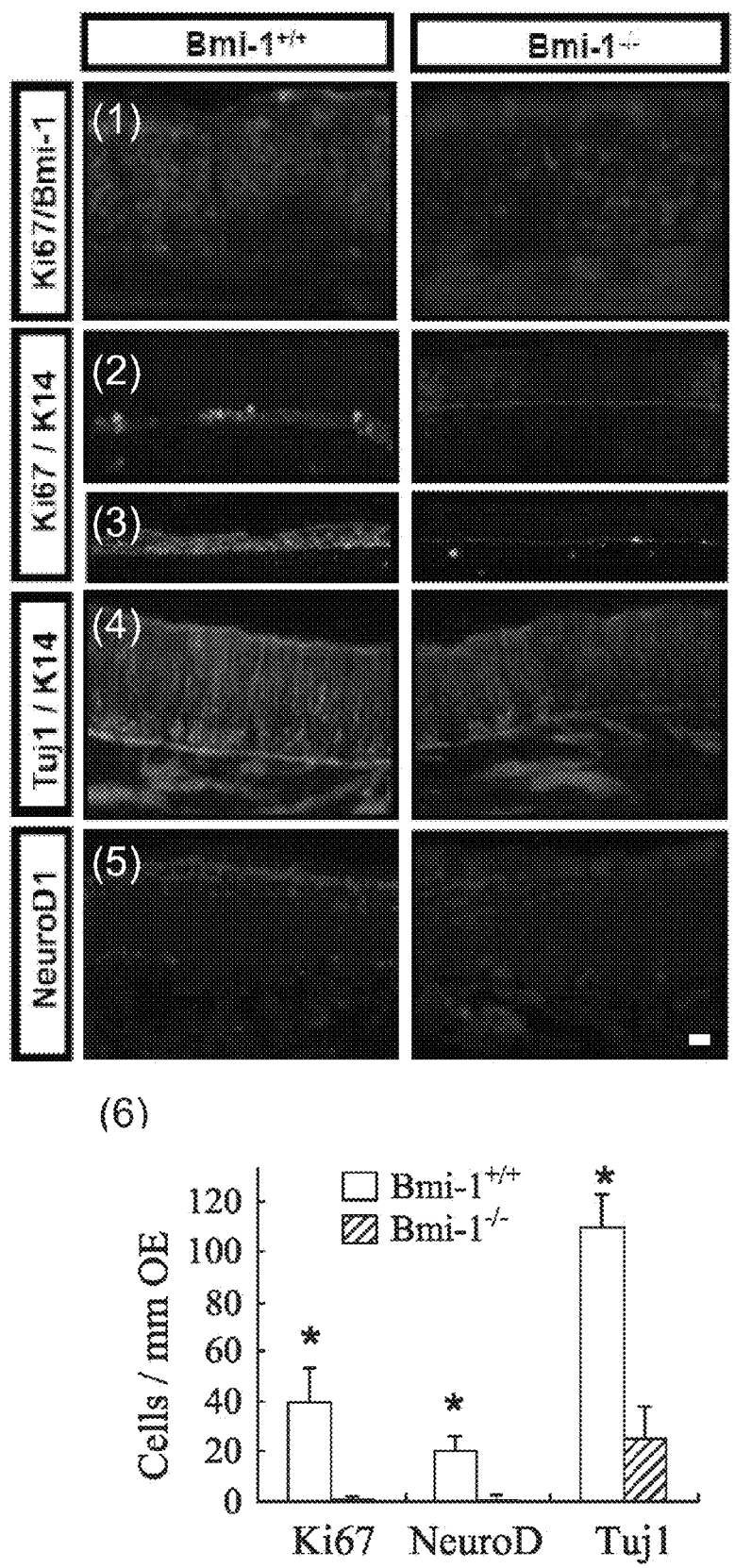
FIG. 8A shows results of effect of the expressions of the Bmi-1 on the APOSCs.

Next, we further discuss the effect of Bmi-1 on the APOSCs. The APOSCs isolated from the olfactory mucosa tissues of Bmi-1$^{+/+}$ mice and the olfactory mucosa tissues of Bmi-1$^{-/-}$ mice are subjected to immunocytochemistry analysis for detecting the expression of Bmi-1 and the expression of the cell proliferation marker Ki67. FIG. 8A-(1) shows the results of the expression of the Bmi-1 and the expression of the Ki67 in the olfactory mucosa tissues of Bmi-1$^{+/+}$ mice and the olfactory mucosa tissues of Bmi-1$^{-/-}$ mice, wherein the green fluorescence represents signal of Bmi-1, and the red fluorescence represents signal of Ki67. The expression of the Bmi-1 and the expression of the Ki67 are not detected in the olfactory mucosa tissues of Bmi-1$^{-/-}$ mice, but the expression of the Bmi-1 and the expression of the Ki67 can be observed in the olfactory mucosa tissues of Bmi-1$^{+/+}$ mice. These results indicate that Bmi-1-expressing basal cells have proliferative activity.

Therefore, we further pursue whether the Bmi-1 is required for self-renewal of the APOSCs within their nature niche. The olfactory neuroepithelium of Bmi-1$^{+/+}$ mice and Bmi-1$^{-/-}$ mice are under an induced injury test respectively, and then observing whether the expression of the Bmi-1 could affect the self-renewal of the APOSCs. The induced injury test is performed by intraperitoneal injection of 50 µg of methimazole (Sigma) per g of animal weight into the mice. The olfactory mucosa tissue is fixed at 3 days following methimazole injection and then subjected to the immunocytochemistry analysis for detecting the expression of the cell proliferation marker Ki67, the HBC marker K14 and the neuronal markers Tuj-1 and NeuroD1. The proliferation of the basal cells is used as an indication for self-renewing APOSCs. Please refer to FIGS. 8A-(2) to 8A-(6), the olfactory mucosa tissues in FIG. 8A-(2) are uninjured, the olfactory mucosa tissues in FIG. 8A-(3) are methimazole-injured, wherein the green fluorescence represents signal of the Ki67, and the red fluorescence represents signal of the K14. FIG. 8A-(4) is the result of double-labeled immunohistochemistry analysis for the Tuj1 and the K14, wherein the green fluorescence represents signal of the Tuj1, the red fluorescence represents signal of the K14, and the blue fluorescence represents signal of DAPI. FIG. 8A-(5) is the result of immunohistochemistry analysis for the NeuroD1, wherein the green fluorescence represents signal of the NeuroD1, and the blue fluorescence represents signal of DAPI. FIG. 8A-(6) is a statistical chart of the staining results of FIGS. 8A-(3) to 8A-(5), wherein * represents P <0.05. In FIG. 8A-(2), only scarce spontaneous cell proliferation is observed among K14$^+$-basal cells. In FIGS. 8A-(3) to 8A-(6), under the induced injury test, chemical insult such as methimazole cause destruction of olfactory neurons, which stimulate the basal cells proliferation and differentiation to replace the neuron loss. Compared with the Bmi-1$^{+/+}$ olfactory mucosa tissue, the number of proliferated APOSCs in the Bmi-1$^{-/-}$ olfactory mucosa tissue is significantly decreased after treating induced injury test. As shown in statistical results of the number of Ki67$^+$K14$^+$ cells, at 3-days post injury, 79% Bmi-1$^{+/+}$ basal cells underwent proliferation, while just 32% Bmi-1$^{-/-}$ basal cells could be stimulated to proliferate. Accordingly, there are significant reductions of immature sensory neurons (Tuj-1$^+$ cells), committed neuronal precursors (NeuroD1$^+$ cells), as well as morphology changes in Bmi-1$^{-/-}$ olfactory mucosa tissue.

Figure 8B:
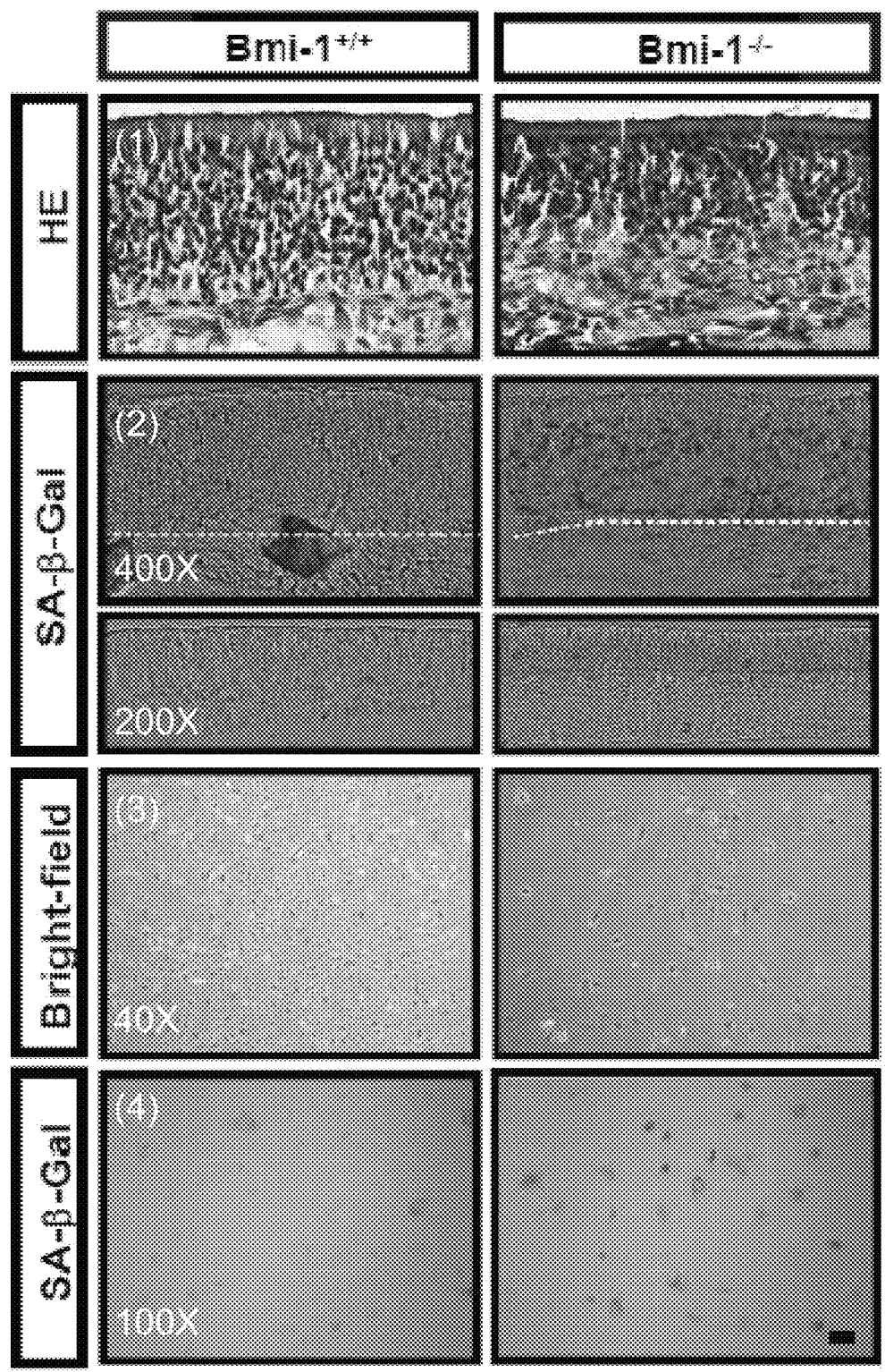
FIG. 8B shows analytical results of a senescence-associated β-galactosidase assay.
Figure 8D:
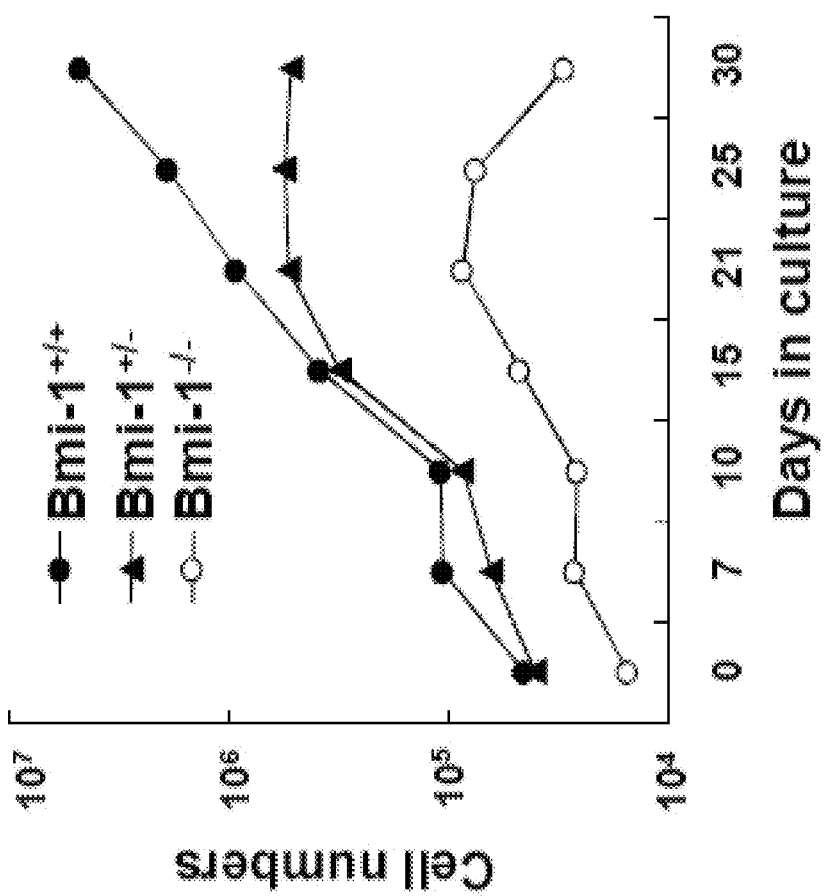
FIG. 8D shows the analytical result of the PI measurement of Bmi-1$^{+/+}$ APOSCs and Bmi-1$^{-/-}$ APOSCs.
Figure 8C:
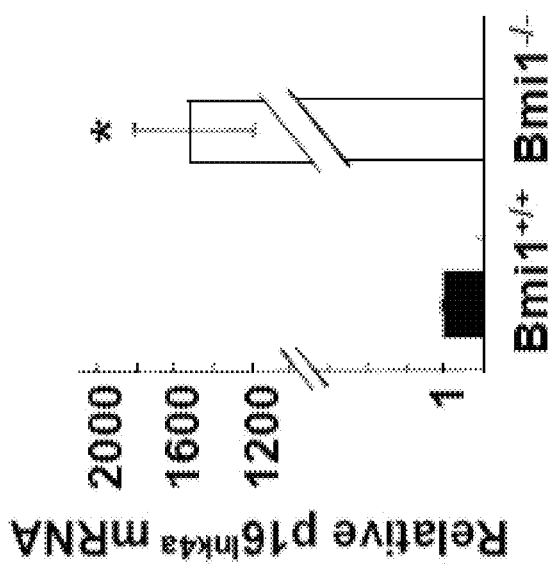
FIG. 8C shows quantitative results of RT-PCR analysis of $p16^{Ink4a}$ in Bmi-1$^{+/+}$ olfactory mucosa tissues and Bmi-1$^{-/-}$ olfactory mucosa tissues.

It has been suggested that Bmi-1 is required for the maintenance of adult stem cells in other tissues partly through suppressing premature cellular senescence and abnormal cell death. To assess whether Bmi-1 plays the same role in the APOSCs, a senescence biomarker, β-galactosidase activity at pH 6, is detected upon the Bmi-1$^{+/+}$ olfactory mucosa tissue and the Bmi-1 olfactory mucosa tissue. FIGS. 8B-(1) to 8B-(3) show analytical results of a senescence-associated (SA) β-galactosidase (β-Gal) assay. FIG. 8B-(1) shows Hematoxylin/Eosin (H&E)-stained olfactory mucosa tissues. FIG. 8B-(2) shows SA-β-Gal-stained adult (8-weeks) olfactory mucosa tissue, wherein blue staining shows SA-β-Gal activity, and the dotted line indicates the basal membrane. In FIG. 8B, apparent senescence phenotype revealed by blue staining is observed in Bmi-1$^{-/-}$ APOSC-residing basal membrane and olfactory neurons, whereas less blue staining cells shown in the Bmi-1$^{+/+}$ olfactory mucosa tissue. FIG. 8C shows quantitative results of RT-PCR analysis of p16$^{Ink4a}$ in Bmi-1$^{+/+}$ olfactory mucosa tissues and Bmi-1$^{-/-}$ olfactory mucosa tissues, wherein * represents P<0.05. P16$^{Ink4a}$ gene is a gene that plays an important role in cell cycle regulation, cell proliferation, differentiation and apoptosis. The p16$^{Ink4a}$ is involved in the induction of senescence. In FIG. 8C, the up-regulation of p16$^{Ink4a}$ in the Bmi-1$^{-/-}$ olfactory mucosa tissue is striking.

Next, we examine the phenotype of Bmi-1$^{+/+}$ APOSCs and Bmi-1$^{-/-}$ APOSCs in this example. We isolate the APOSCs from the Bmi-1$^{+/+}$ mouse olfactory mucosa tissue (the Bmi-1$^{+/+}$ APOSCs) and the Bmi-1$^{-/-}$ mouse olfactory mucosa tissue (the Bmi-1$^{-/-}$ APOSCs), respectively. The Bmi-1$^{+/+}$ APOSCs and the Bmi-1$^{-/-}$ APOSCs are performed the SA-β-Gal assay to detect their senescence biomarker β-Gal activity at pH 6. Please refer to FIGS. 8B-(3), 8B-(4) and 8D, FIG. 8B-(3) is the micrograph of the APOSCs under the bright field, FIG. 8B-(4) shows SA-β-Gal-stained APOSCs, and FIG. 8D shows the analytical result of the PI measurement of the Bmi-1$^{+/+}$ APOSCs and the Bmi-1$^{-/-}$ APOSCs. In FIGS. 8B-(3), 8B-(4) and 8D, in vitro cultivated Bmi-1$^{-/-}$ APOSCs show premature senescence since they stop dividing after 21 days, obtain flattened/enlarged cell appearance, and 40%±5% Bmi-1$^{-/-}$ APOSCs show abundant blue staining for the SA-β-Gal expression. In contrast, the Bmi-1$^{+/+}$ APOSCs keep dividing beyond 32 days, mostly remain spindle-shaped morphology, and just 16%±1% Bmi-1$^{+/+}$ APOSCs reveal the SA-β-Gal expression.

Figure 8E:
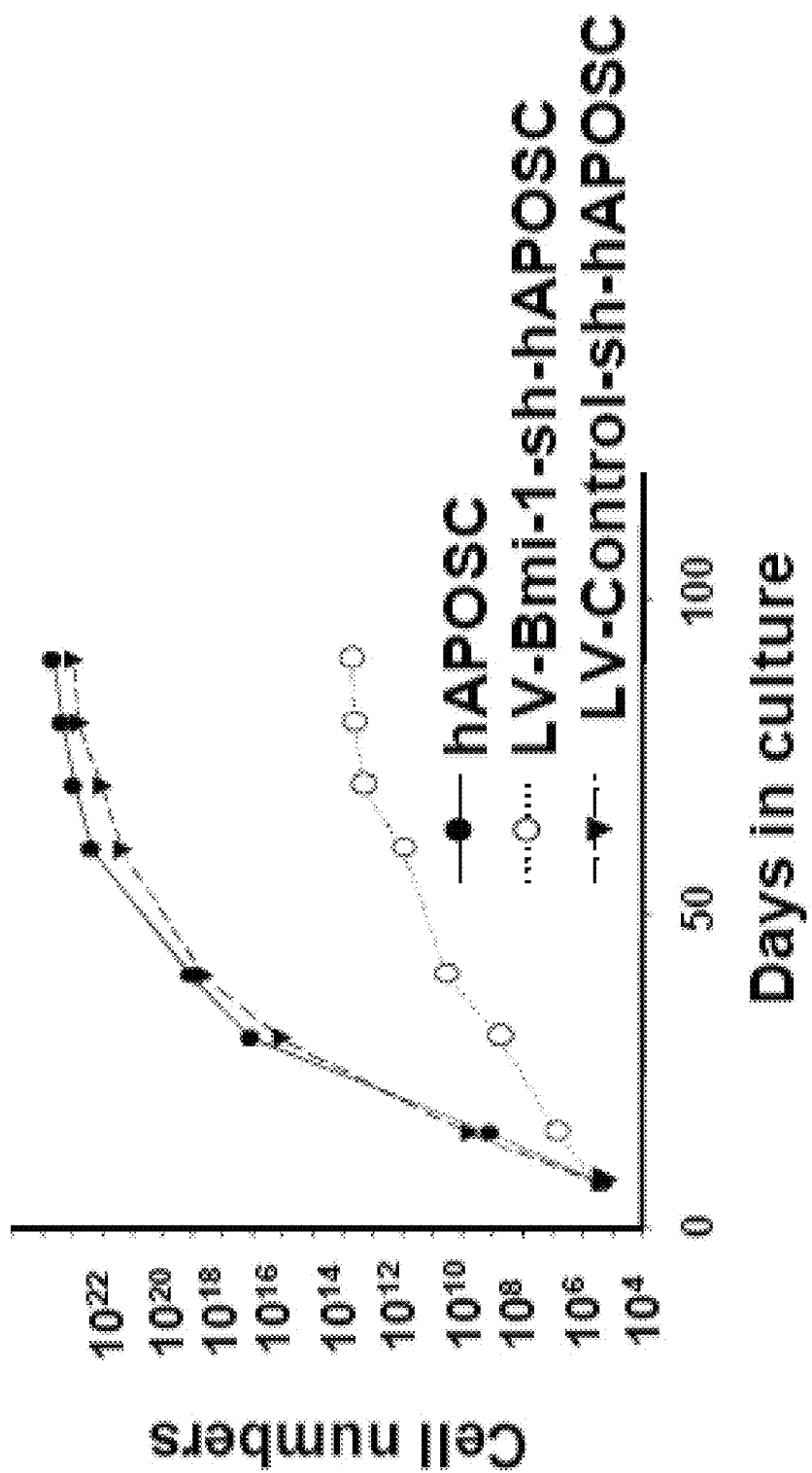
FIG. 8E shows the analytical result of the PI measurement of the human APOSCs transduced with shRNA.

To prove that the expression of the Bmi-1 will affect the APOSCs senescence, shRNA for Bmi-1 (LV-Bmi-1-sh; sc-29815-V, Santa Cruz Biotechnology) is achieved by lentiviral delivery into the human APOSCs (LV-Bmi-1-sh-hAPOSC) to knockdown the expression of the Bmi-1 in the APOSCs. A control group is transduced with control shRNA (LV-control-sh; sc-108080, Santa Cruz Biotechnology) into the human APOSCs (LV-control-sh-hAPOSC) in this example. FIG. 8E shows the analytical result of the PI measurement of human APOSCs transduced with shRNA. In FIG. 8E, when the Bmi-1 in the human APOSCs is down-regulated by lenti-virus-shRNA, the long-term expansion ability of the LV-Bmi-1-sh-hAPOSC is significantly reduced. Besides, we do not detect increased apoptosis in the Bmi-1$^{-/-}$ olfactory mucosa tissue by a TUNEL assay (data not shown). Above findings suggest an essential role for the Bmi-1 in regulating the APOSCs self-renewing through suppressing their premature cellular senescence, but not apopotosis.

II. The APOSCs of the Present Disclosure Used for Treating the Brain Tissue Damage The data of the first part examples demonstrate that the APOSCs have self-renewal capability and pluripotent capability, as well as neurogenic ability and angiogenic ability. In the second part examples, we further discuss the effect on the APOSCs used for treating the brain tissue damage.

2.1. Intracerebral mAPOSC Transplantation Reduces Infarct Volume and Improves Neurological Behavior after Cerebral Ischemia The cell transplantation is performed by stereotaxically injecting 10$^6$ cells of the mAPOSC-GFP into the brain tissue of the stroke mice at 7 days post cerebral ischemia/reperfusion. The infarct volume of the stroke mice is examined four weeks post the cell transplantation. In addition, neurological deficits modality for assessing neurological behavioral is performed before and after the stroke to evaluate the neurological recovery.

Figure 9B:
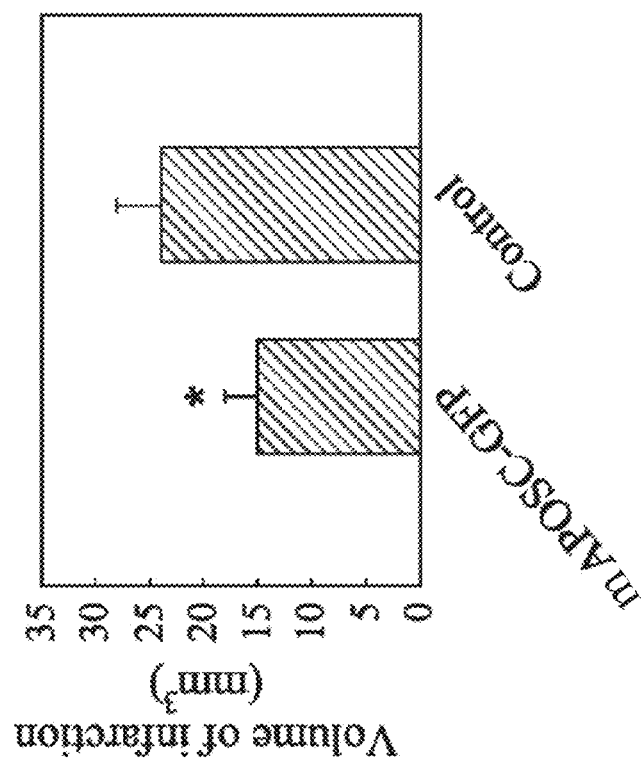
FIG. 9B is a statistical result chart of FIG. 9A.
Figure 9A:
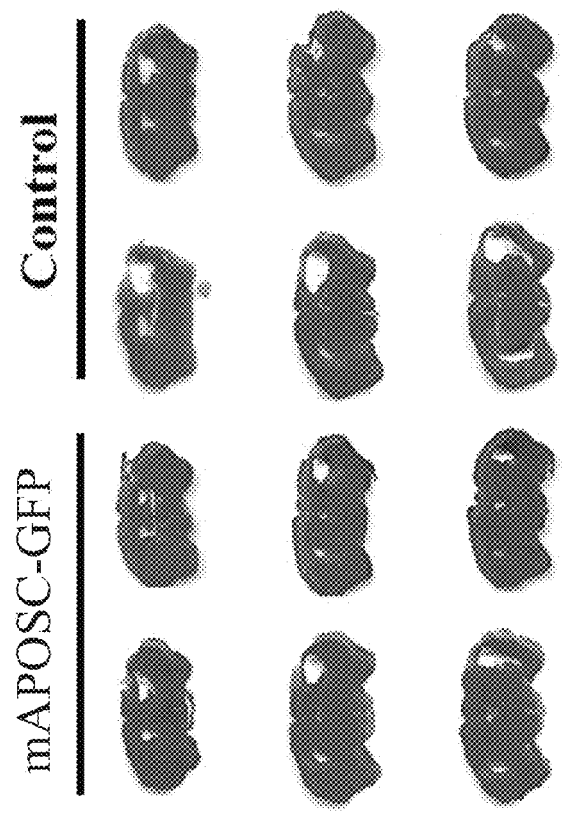
FIG. 9A is photograph showing infarct volume in brain tissues of stroke mice transplanted with the APOSCs.

The stroke mice transplanted with the mAPOSC-GFP are sacrificed at 28 days after the cell transplantation to obtain their brain tissue. A series of 20-μm thick coronal sections with a 200-μm interval are cut by a cryostat. Brain tissue sections are stained with H&E staining. To measure the infarct area in the right cortex, we subtract the noninfarcted area in the right cortex from the total cortical area of the left hemisphere. The area of infarct is drawn manually from slice to slice, and the volume is then calculated by internal volume analysis software (NIH Image J). FIG. 9A is photograph showing infarct volume in the brain tissues of the stroke mice transplanted with the APOSCs. FIG. 9B is a statistical result chart of FIG. 9A. In FIGS. 9A and 9B, more reduction of the infarct volume is found in the mAPOSC-GFP-transplanted stroke mice than control mice (the stroke mice without the mAPOSC-GFP transplantation).

Neurological behavioral assessments are performed between 6 and 28 days after the cerebral ischemia/reperfusion. The neurological deficits modality measures locomotor activity of the mice. The locomotor activity test is measured for about 2 hours using VersaMax Animal Activity Monitoring System (Accuscan Instruments), which contains 16 horizontal infrared sensors and 8 vertical infrared sensors. The vertical sensors are situated 10 cm above the chamber floor and the locomotor activity is quantified by a number of a beam broken by the mouse's movement in the chamber. Three vertical-movement parameters are measured: (i) a vertical activity (ii) a vertical time (iii) a number of vertical movements by the manufacturer's instruction.

Figure 9D:
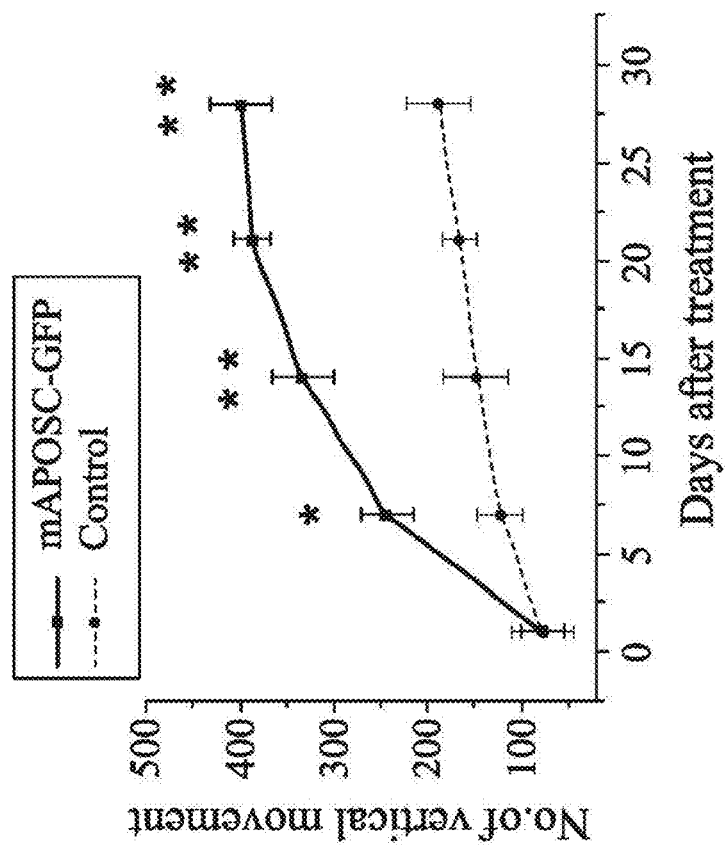
FIG. 9D shows analytical results of a number of the vertical movements in the locomotor activity test.
Figure 9C:
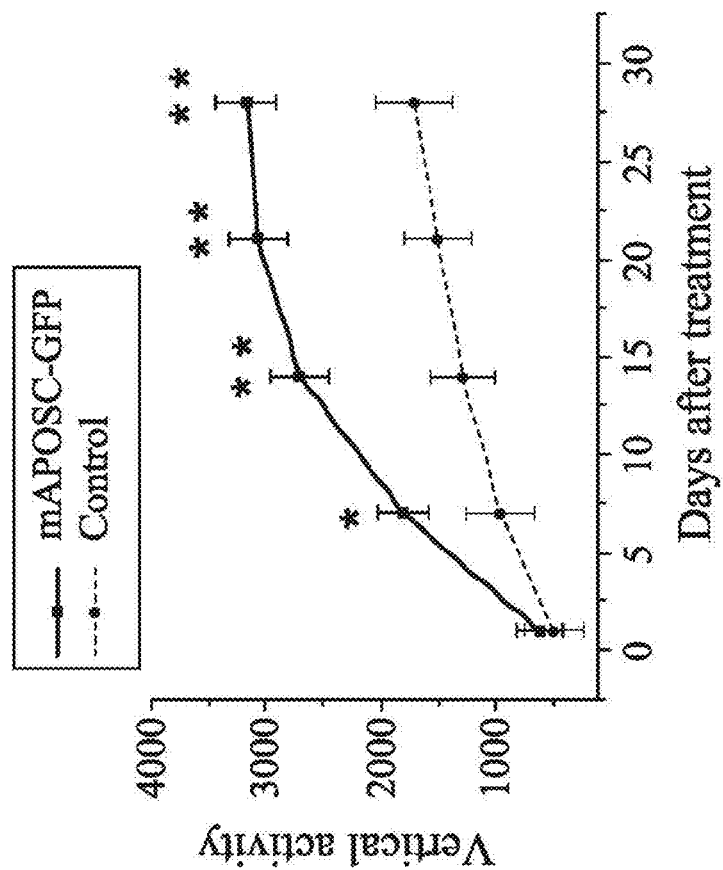
FIG. 9C shows analytical results of a vertical activity in a locomotor activity test.
Figure 9E:
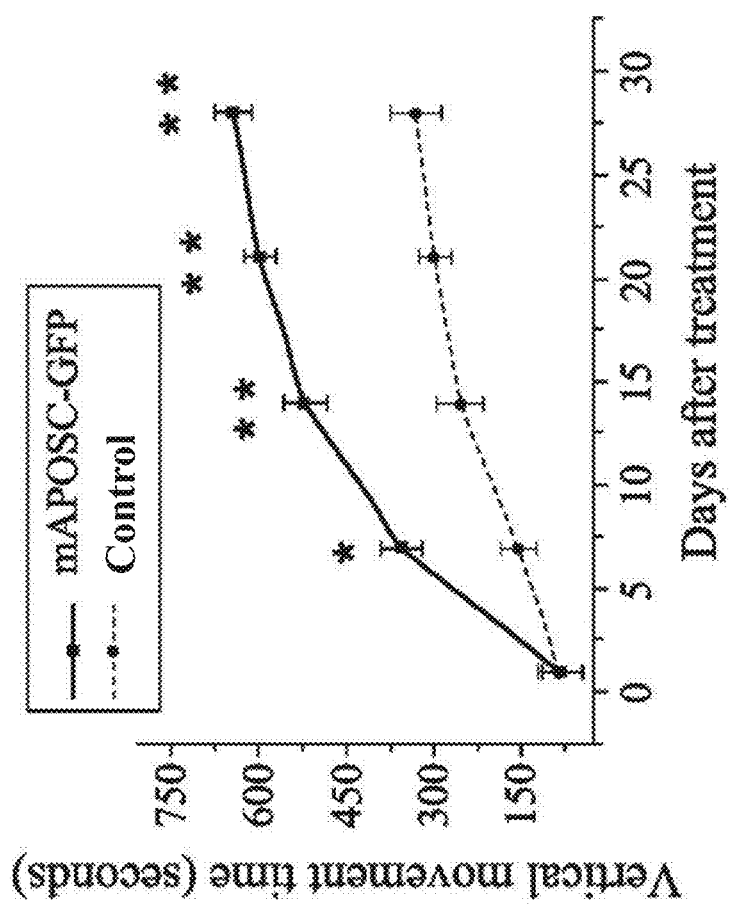
FIG. 9E shows analytical results of a vertical movement time in the locomotor activity test.

FIG. 9C shows analytical results of the vertical activity in the locomotor activity test. FIG. 9D shows analytical results of the number of the vertical movements in the locomotor activity test. FIG. 9E shows analytical results of the vertical movement time in the locomotor activity test. In FIGS. 9C to 9E, locomotor activity including vertical activity, the number of vertical movements and vertical movement time significantly increase between 6 and 28 days after cerebral ischemia in the stroke mice receiving the murine APOSC transplantation, compared with the control mice.

Figure 9F:
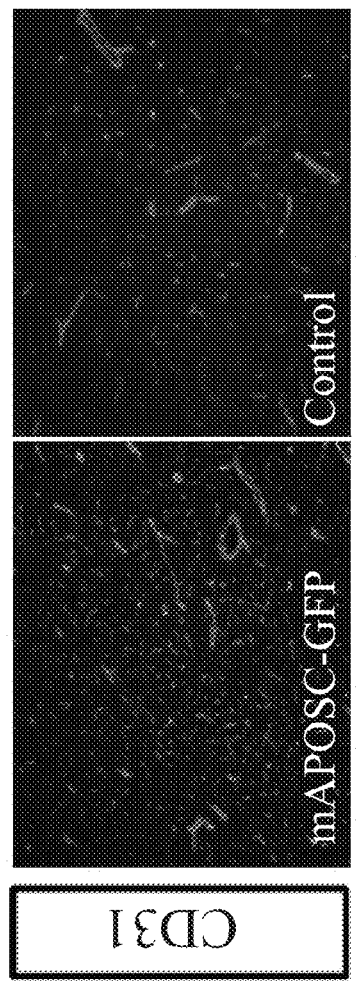
FIG. 9F shows analytical results of CD31 expressions in the brain tissues of the stroke mice transplanted with murine APOSCs.
Figure 9F:
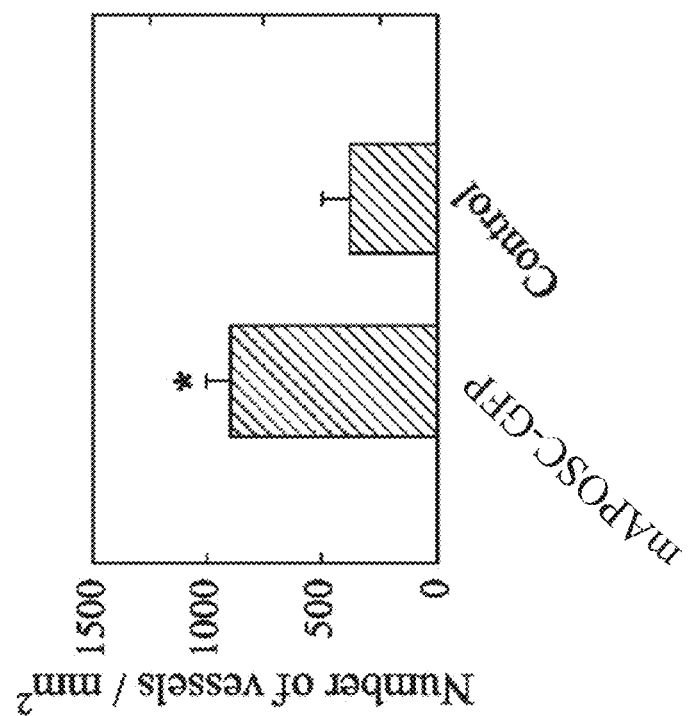

To determine whether the APOSCs implantation induces the angiogenesis in brain of the stroke mouse, blood vessel density is quantitatively measured by CD31 immunoreactivity. FIG. 9F shows analytical results of CD31 expressions in the brain tissues of the stroke mice transplanted with the murine APOSCs. In FIG. 9F, the amount of neovasculature in the penumbric area of the stroke mice transplanted with the mAPOSC-GFP significantly increase compared with that of the control mice.

These results indicate that the APOSCs transplantation can significantly improve the neurological function of the stroke mice. The implanted APOSCs significantly migrate into the brain of the stroke mice, and the APOSCs transplantation leads to migration of the APOSCs to ischemic sites to repair damaged neuron.

2.2. Pilot the APOSC Implantation in Stroke Patients

To address the safety and feasibility of autologous APOSCs implantation for the clinical treatment of stroke-induced neurological dysfunction, we started recruiting patients in a clinical trial. The clinical trial is approved by the Institutional Review Board (IRB) of the China Medical University Hospital, Taichung, Taiwan. Six patients are enrolled in the clinical trial under the approval of Taiwan Food and Drug Administration (TFDA).

Figure 10A:
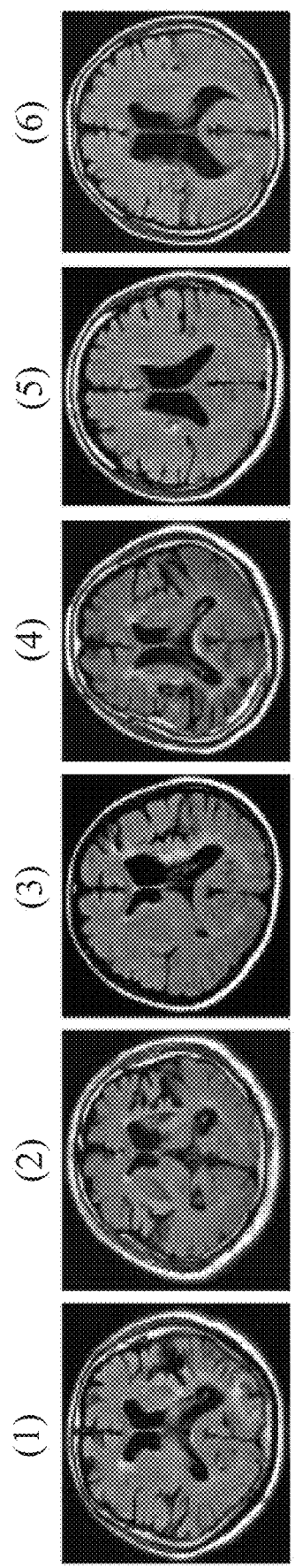
FIG. 10A shows magnetic resonance imaging (MRI) data of subjects.
Figure 10B:
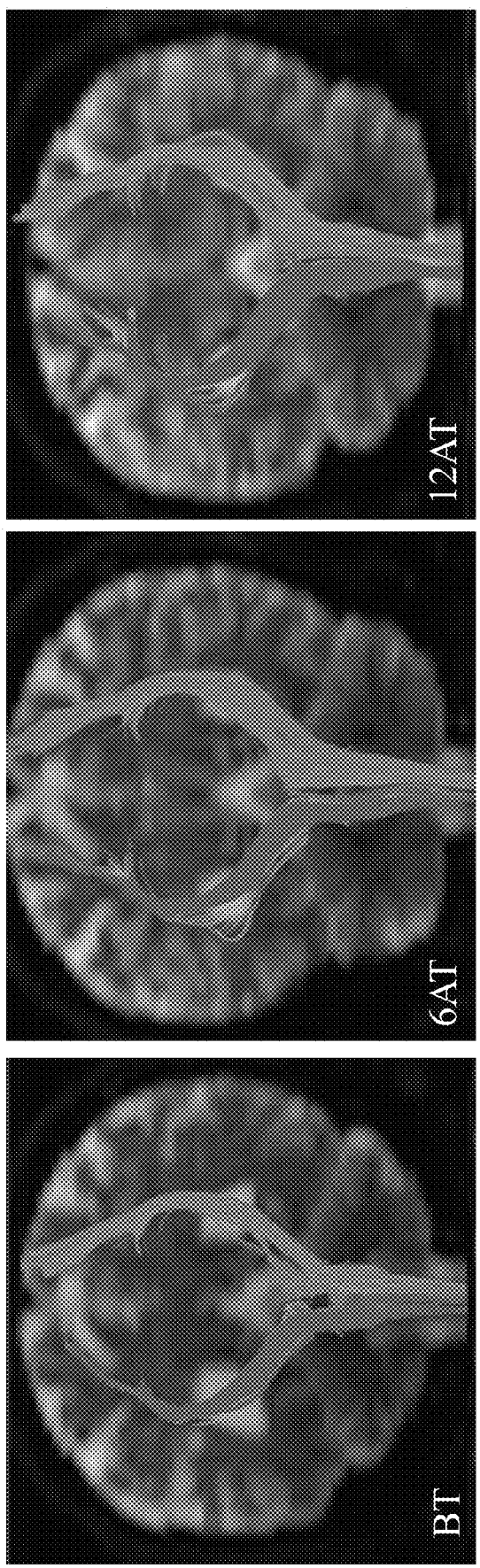
FIG. 10B shows MRI protocol for processing the diffusion tensor image (MRI-DTI) data of one of the subjects.

Please refer to Table 1 and FIG. 10A. Table 1 shows characteristics of the APOSCs implantation in each subject, wherein Rt represents right limbs, Lt represents left limbs, and IC represents intracerebral. FIG. 10A shows magnetic resonance imaging (MRI) data of the subjects. The subjects of the clinical trial are selected from patients suffered from an old stroke on the weight image (M1 and M2) of MRI (excluding hemorrhagic stroke) and onset on the National Institute of Health stroke scale (NIHSS) from 5 to 15 scales between 35 and 70 years of age. The autologous APOSCs are isolated from autologous olfactory mucosa tissues of the subject. The number of the implanted APOSCs is $2 \times 10^6$, and all subjects are followed every 1 to 3 months in the clinic trail for 12 months after the implantation. An independent safety committee monitors the results of the clinic trial including frequency of adverse reaction (AEs). The primary end points evaluated by clinical scoring of Fugl-Meyer test (FMT) are determined at baseline, 6 and 12 months after the APOSCs implantation. By following up to 12 months after the implantation, six subjects experience no systemic or local adverse events, thus providing preliminary evidence of the safety and feasibility of this therapeutic protocol.

the FA is between zero and one, wherein the larger value of the FA represents more the water molecules diffuse in a single direction. In FIG. 10B, the value of the FA of the subject before the APOSCs implantation (BT) is 0.47, the value of the FA of the subject at 6 months after the APOSCs implantation (6-AT) is 0.39, and the value of the FA of the subject at 12 months after the APOSCs implantation (12-AT) is 0.33. By comparing the value of the FA before and 12 months after the APOSCs implantation shows prominent increase in the fiber numbers of cortico-spinal tract (CST).

Figure 10C:
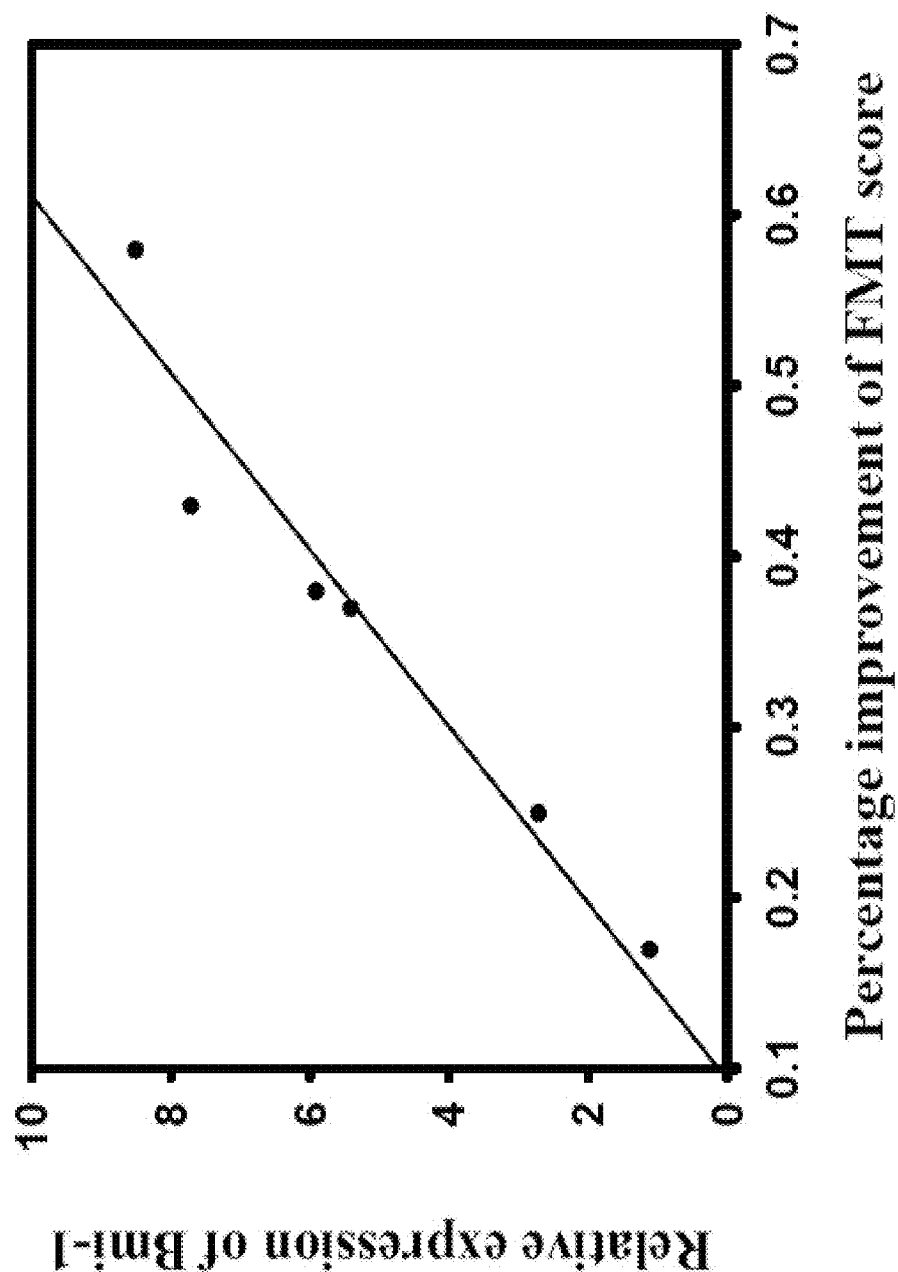
FIG. 10C shows a correlation diagram between relative expression of the Bmi-1 and percentage change of Fugl-Meyer test score.

Moreover, a simple linear correlation analysis is calculated to show the relationship between clinical improvement and the expression of the Bmi-1 in the APOSCs. FIG. 10C shows a correlation diagram between relative expression of the Bmi-1 and percentage change of Fugl-Meyer test (FMT) score. The percentage change of the FMT score measures at 12 months after cell implantation strongly correlated with the relative expression of Bmi-1 (correlation coefficient: $r=0.97$; $p<0.001$). It indicates that subjects with high expression of the Bmi-1 in their autologous APOSCs have significantly better clinical outcome than those with low expression of the Bmi-1 in their autologous APOSCs.

To sum up, the present disclosure provides the adult pluripotent olfactory stem cell (APOSC) expresses the Bmi-1 on its cell surface and expresses pluripotent markers Oct-4, Sox-2, Nanog and SSEA-4. The APOSC has self-renewal capability and pluripotent differentiation capability. The method for obtaining a plurality of pluripotent APOSCs of the present disclosure can isolate a plurality of cells that express Oct-4, Sox-2, Nanog and SSEA-4 from the cell mixture provide from the olfactory tissue of the mammal, or further isolate the Bmi-1 positive cells from the mammalian olfactory tissue cell mixture to obtain the pluripotent adult olfactory stem cells. Therefore, the method can quickly and specifically screen the pluripotent adult olfactory stem cells.

TABLE 1

Characteristics of the APOSC implantation in each subject

| Subject | 1 | 2 | 3 | 4 | 5 | 6 |
|---|---|---|---|---|---|---|
| Symptoms and signs | Rt hemiparesis | Rt hemiparesis | Rt hemiparesis | Lt hemiparesis | Lt hemiparesis | Lt hemiparesis |
| Stroke history (months) | 51 | 11 | 12 | 16 | 20 | 29 |
| No. of injected cells | $2 \times 10^6$ | $2 \times 10^6$ | $2 \times 10^6$ | $2 \times 10^6$ | $2 \times 10^6$ | $2 \times 10^6$ |
| Purity of $P^{75+}$ cells | 91.5% | 90.4% | 95.5% | 91.7% | 91% | 91% |
| No. of IC trajectory | 3 | 3 | 3 | 3 | 3 | 3 |

FIG. 10B shows MRI protocol for processing the diffusion tensor image (MRI-DTI) data of one of the subjects, wherein the MRI-DTI data can evaluate tissue structures of the brain and directions of the nerve fibers by observing the directions of diffusion of water molecules in the brain tissue. The water molecules in the body diffuse freely in three dimensions, but the direction of the diffusion of the water molecules can be affected by permeability of surrounding tissue, axon direction, or intracellular microtubule depolymerization. Therefore, a change of microstructure of white matter can be determined by observing anisotropy of water molecules (whether the water molecule diffuses in a single direction). A fractional anisotropy (FA) can be used to represent diffusion amount of the water molecules and the direction of the diffusion of the water molecules. A value of Furthermore, the APOSCs of the present disclosure can be used in the cell treatment for treating the brain tissue damage. In more details, for treating the brain tissue damage, the APOSCs can improve the neurological function of the subject having the brain tissue damage. The implanted APOSCs can migrate into the damage brain tissue to repair damaged neuron and reduce the infarct volume after the stroke. Therefore, the APOSCs can treat the subject having the brain tissue damage.

Although the present disclosure has been described in considerable detail with reference to certain embodiments thereof, other embodiments are possible. Therefore, their spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for obtaining a plurality of pluripotent adult olfactory stem cells (APOSCs), the method comprising:
   i. isolating the APOSCs, comprising:
      (a) obtaining an olfactory tissue of a mammal;
      (b) culturing the olfactory mucosa tissue obtained from step (a) in a medium containing Dulbecco's Modified Eagle Medium/F12 (DMEM/F12 medium), heparin, bFGF, EGF and an antibiotic for 5-7 days to allow for migration of the cells from the cultured tissue; and
      (c) isolating adherent cells from step (b);
   ii. culturing the isolated APOSCs in a sphere culture medium comprising DMEM/F12 medium, B27 supplement, bFGF, EGF and an antibiotic; and
   iii. collecting the cultured APOSCs that express Bmi-1 (B-lymphoma moloney murine leukemia virus insertion region-1), Oct-4 (Octamer-binding transcription factor 4), Sox-2 (Sex-determining region Y (SRY)-box 2), Nanog, SSEA-4 (Stage-specific embryonic antigen-4), ki67, c-Myc, KLF-4 (Kruppel Like Factor 4), K14 (Cytokeratin 14) and ICAM-1 (Intercellular Adhesion Molecule 1).

2. The method of claim 1, wherein the mammal is a human or a murine.

3. The method of claim 1, wherein the APOSCs is derived from a basal layer of the olfactory tissue.

* * * * *